under 35 U.S.C. 154(b) by 142 days.

(12) United States Patent
Suzuki et al.

(10) Patent No.: US 12,402,848 B2
(45) Date of Patent: Sep. 2, 2025

(54) RADIATION IMAGING APPARATUS, RADIATION DETECTOR, METHOD AND APPARATUS FOR CONTROLLING RADIATION IMAGING APPARATUS, AND PROGRAM FOR THE SAME

(71) Applicant: CANON KABUSHIKI KAISHA, Tokyo (JP)

(72) Inventors: Kai Suzuki, Kanagawa (JP); Yuichi Naito, Kanagawa (JP); Keigo Yokoyama, Kanagawa (JP); Tomoya Suzuki, Tokyo (JP); Akira Tsukuda, Tokyo (JP); Eriko Sato, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 142 days.

(21) Appl. No.: 18/476,158

(22) Filed: Sep. 27, 2023

(65) Prior Publication Data

US 2024/0023914 A1 Jan. 25, 2024

Related U.S. Application Data

(63) Continuation of application No. PCT/JP2022/015490, filed on Mar. 29, 2022.

(30) Foreign Application Priority Data

Mar. 30, 2021 (JP) .................. 2021-058489
Mar. 15, 2022 (JP) .................. 2022-040251

(51) Int. Cl.
*A61B 6/00* (2024.01)
*A61B 6/42* (2024.01)
(Continued)

(52) U.S. Cl.
CPC .......... *A61B 6/4405* (2013.01); *A61B 6/4266* (2013.01); *A61B 6/461* (2013.01); *A61B 6/54* (2013.01); *G01T 1/20182* (2020.05)

(58) Field of Classification Search
CPC ..... A61B 6/4405; A61B 6/4266; A61B 6/461; A61B 6/54; A61B 6/4464; A61B 6/587; A61B 6/547; G01T 1/20182; G01T 1/161
See application file for complete search history.

(56) References Cited

U.S. PATENT DOCUMENTS 7,744,279 B2 * 6/2010 Heath .................. G03B 42/02
378/197
2015/0098551 A1 4/2015 Kwak et al.
(Continued)

FOREIGN PATENT DOCUMENTS

JP 2000023955 A 1/2000
JP 2011125544 A 6/2011
(Continued)

*Primary Examiner* — Kiho Kim
(74) *Attorney, Agent, or Firm* — Canon U.S.A., Inc. IP Division

(57) ABSTRACT

A setting unit configured to set a reference orientation for calculating the orientation of a radiation detector and a reference orientation for calculating the orientation of the radiation generator sets the reference orientations of the radiation detector and the radiation generator in response to determining that a mobile radiography unit equipped with the radiation generator stands still, with the radiation detector housed, to determine whether the radiation generator and the radiation detector are arranged according to the imaging procedure.

28 Claims, 12 Drawing Sheets

(51) Int. Cl.
*A61B 6/46* (2024.01)
*G01T 1/20* (2006.01)

(56) References Cited

U.S. PATENT DOCUMENTS

2020/0046311 A1* 2/2020 Vogelsang ............. A61B 6/582
2020/0107799 A1* 4/2020 Nebosi ................. A61B 6/587
2022/0047233 A1* 2/2022 Spaeth .................... A61B 6/54

FOREIGN PATENT DOCUMENTS

| JP | 2014045939 A | 3/2014 |
| JP | 2015023915 A | 2/2015 |
| JP | 2018007923 A | 1/2018 |

* cited by examiner

RADIATION IMAGING APPARATUS, RADIATION DETECTOR, METHOD AND APPARATUS FOR CONTROLLING RADIATION IMAGING APPARATUS, AND PROGRAM FOR THE SAME

CROSS-REFERENCE TO RELATED APPLICATIONS

This application is a Continuation of International Patent Application No. PCT/JP2022/015490, filed Mar. 29, 2022, which claims the benefit of Japanese Patent Application No. 2021-058489, filed Mar. 30, 2021, and No. 2022-040251, filed Mar. 15, 2022, all of which are hereby incorporated by reference herein in their entirety.

TECHNICAL FIELD

The present invention relates to a radiation imaging apparatus, a radiation detector, a method and an apparatus for controlling the radiation imaging apparatus, and a program for the same.

BACKGROUND ART

At present, flat panel detectors (FPDs) made of a semiconductor material are in widespread use as radiation detectors for use in medical diagnostic imaging and nondestructive examinations using radiation such as X rays. Radiation imaging apparatuses are in use in which such a radiation detector and a radiation generator or the like are combined.

As a function of such a radiation imaging apparatus, a function for supporting positioning of the radiation field surface of radiation emitted from a radiation generator and the incident surface of the radiation detector by calculating the orientations of the radiation generator and the radiation detector and displaying the orientations is in practical use.

An example of a method for calculating the orientations of the radiation generator and the radiation detector is calculating the orientations, with an acceleration sensor or a gyroscope provided at each of the radiation generator and the radiation detector, from accelerations, which are output values from the acceleration sensors, or angular velocities, which are output values from the gyroscopes.

For example, the calculation of the orientation using the gyroscope is made by cumulating (integrating) the angular velocities in a minute time obtained by the gyroscope. The calculation of the orientation using the acceleration sensor is made by cumulating accelerations obtained by the acceleration sensor to calculate a speed at a certain time and further cumulating the speeds again to convert it to a displacement (position).

However, what can be calculated by the above method is the sum of the orientation changes, and the current accurate orientation cannot be calculated unless a reference orientation at a certain time (hereinafter, referred to as reference orientation) is known.

To avoid such a problem, PTL 1 discloses a radiation imaging apparatus including an input unit for setting a reference orientation and a positioning ruler, which is a structure for positioning. The user of the radiation imaging apparatus can set the reference orientation by providing an instruction for setting the reference orientation (calibration processing) via the input unit when the radiation detector abuts on the positioning ruler.

For example, for supporting the positioning of a radiation generator and a radiation detector, PTL 2 discloses a technique for setting vectors based on the orientation information on a radiation generator and radiation detectors in an environment in which a plurality of radiation detectors is used. This allows selection of a radiation detector whose vector forming with the vector of the radiation generator is less than a predetermined value.

CITATION LIST

Patent Literature

PTL 1 Japanese Patent Laid-Open No. 2018-007923
PTL 2 US Patent Application, Publication No. 2015/0098551

However, the radiation imaging apparatus disclosed in PTL 1 requires the user to provide an instruction via the input unit when setting the reference orientation, complicating the procedure for use.

In some medical front, the radiation detector is used in a bag from the aspect of good hygiene. This makes it difficult for the user to visually determine the front and the back of the radiation detector. In applying the technique of PTL 2 in such a situation, when a notification that the angle of the radiation generator and the angle of the radiation detector are mismatched is given, it cannot be determined whether the angles are mismatched or the angles are matched but the back of the radiation detector faces. If the user visually determines that the orientations are coincide and applies radiation, with the back of the radiation detector facing, an image not suitable for diagnosis is formed.

SUMMARY OF INVENTION

A first aspect of the present invention provides a radiation imaging apparatus configured to set reference orientations for calculating the orientations of the radiation detector and the radiation generator without the user, such as an operator, performing complicated operations.

A second aspect of the present invention provides a radiation imaging apparatus configured to notify the user whether the radiation detector is positioned relative to the radiation generator according to the imaging procedure in matching the angles using the orientation information on the radiation generator and the radiation detector.

A radiation imaging apparatus according to the first aspect includes a radiation detector configured to detect radiation, a mobile radiography unit configured to house the radiation detector and including a radiation generator, and a setting unit configured to set at least one of a reference orientation of the radiation detector for calculating an orientation of the radiation detector and a reference orientation of the radiation generator for calculating an orientation of the radiation generator, wherein the radiation imaging apparatus is configured to perform radiation imaging to generate an image based on the radiation, and wherein the setting unit performs the setting in response to determining that the mobile radiography unit stands still, with the radiation detector housed in the mobile radiography unit.

A radiation imaging apparatus according to the second aspect includes a radiation detector configured to detect radiation, a mobile radiography unit configured to house the radiation detector and including a radiation generator, an orientation acquisition unit configured to acquire relative relationship between an orientation of the radiation generator and an orientation of the radiation detector, a first orientation measuring unit configured to measure information on the orientation of the radiation generator, and a second orientation measuring unit configured to measure information on the orientation of the radiation detector, wherein the orientation acquisition unit acquires the relative relationship from an angle formed between a first normal vector and a second normal vector, the first normal vector being aligned with a direction of the radiation from the radiation generator and being based on a value measured by the first orientation measuring unit, the second normal vector being perpendicular to a detector plane of the radiation detector and being based on a value measured by the second orientation measuring unit.

Using a radiation imaging apparatus according to an embodiment of the present invention allows setting reference orientations for calculating the orientations of the radiation detector and the radiation generator without the need for a user, such as an operator, to perform complicated operations. This also allows notifying the user of the result of determination of the arrangement of the radiation generator and the radiation detector in positioning the radiation detector and the radiation generator.

Further features of the present invention will become apparent from the following description of exemplary embodiments with reference to the attached drawings.

DESCRIPTION OF EMBODIMENTS

The present invention will be described hereinbelow using exemplary embodiments with reference to the accompanying drawings. It is to be understood that the following embodiments do not limit the invention according to the claims. Although the embodiments describe a plurality of characteristics, not all of the plurality of characteristics is absolutely necessary for the invention and may be freely combined. In the accompanying drawings, like or similar components are given like reference signs, and redundant descriptions will be omitted. The term "radiation" is typically X-rays, but may include α rays, β rays, γ rays, particle rays, and cosmic rays.

First Embodiment

Figure 1A:
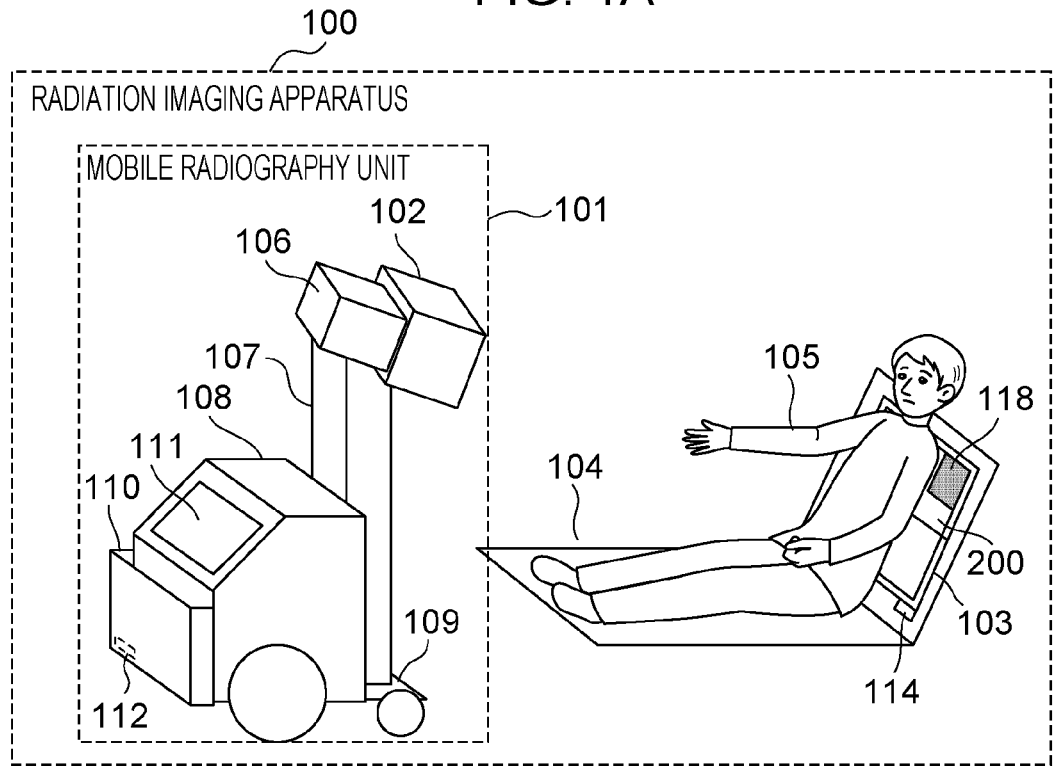
FIG. 1A is a diagram illustrating a configuration example of a radiation imaging apparatus and a radiation generator according to a first embodiment of the present invention.

FIG. 1A is a conceptual diagram illustrating a configuration example of a radiation imaging apparatus 100 according to a first embodiment of the present invention.

A mobile radiography unit 101 is a movable truck with wheels or the like, on which a radiation generator 102 is mounted. The mobile radiography unit 101 is used for radiation imaging together with a flat panel detector (FPD) 103 (an example of a radiation detector). The FPD 103 is disposed on the back of a subject 105 on a bed 104 for radiation imaging. The FPD 103 generates a radiological image of the subject 105 based on the radiation radiated from the radiation generator 102 and applied to the radiation detecting unit 200 through the subject 105.

The radiation detecting unit 200 includes a scintillator that converts the radiated radiation to light and a pixel array in which photoelectric conversion elements that convert light from the scintillator to electrical charge are disposed in a two-dimensional array. The electrical charge based on the radiation, generated by the radiation detecting unit 200, flows to a read circuit (not shown) in sequence by scanning the pixel array with a drive circuit (not shown) to generate an image based on the radiation. The image generated by the radiation detecting unit 200 is sent to a second control unit 203 and is processed as necessary by the second control unit 203.

The mobile radiography unit 101 further includes, in addition to the radiation generator 102, a first arm 106 and a second arm 107 that support the radiation generator 102. The mobile radiography unit 101 further includes a casing 108, a base 109, and an FPD housing unit 110.

In this embodiment, the first arm 106 connects to the radiation generator 102 and the second arm 107, and the second arm 107 connects to the first arm 106 and the base 109. The casing 108 has a first display 111 fitted on the outside and contains a battery (not shown), a high-voltage generator (not shown), a first control unit 201 shown in FIG. 2 (not shown in FIGS. 1A and 1B), and a first information transmitter and receiver 202 (not shown in FIGS. 1A and 1B).

The FPD housing unit 110 is a pocket provided at the mobile radiography unit 101 to mount the FPD 103 on the mobile radiography unit 101. The FPD housing unit 110 includes a first housing determination unit 112 for determining whether the FPD 103 is housed. Connecting the first housing determination unit 112 and a second housing determination unit 114, described later, allows a determination whether the FPD 103 is housed in the FPD housing unit 110.

The FPD housing unit 110 serves as a reference for calculating the position of the FPD 103, described later, so that the FPD housing unit 110 has a positioning mechanism for positioning the FPD 103. If the first housing determination unit 112 and the second housing determination unit 114, described later, are connected by an electrical connector, the electrical connector may also serve as a positioning mechanism.

The first display 111 is formed of a touch panel so as to accept user's input. Other examples of the input device that accepts user's input include a keyboard, a mouse, a speech recognition device, and a user's posture recognition device using a distance sensor. The FPD 103 has a built-in battery (not shown) so as to be operated using the electric power of the battery.

Figure 1B:
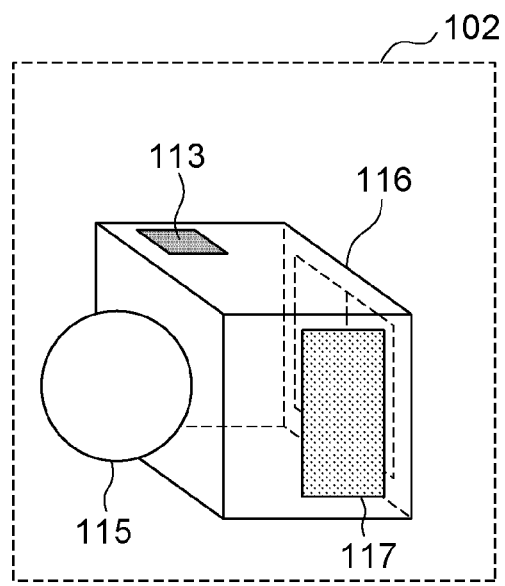
FIG. 1B is a diagram illustrating a configuration example of the radiation imaging apparatus and the radiation generator according to the first embodiment.

The FPD 103 of this embodiment includes a second orientation measuring unit 118, the second housing determination unit 114 provided on the FPD 103 side, a second control unit 203 (not shown in FIGS. 1A and 1B) and a second information transmitter and receiver 204 (not shown in FIGS. 1A and 1B). The second orientation measuring unit 118 in this embodiment is an acceleration sensor. The orientation measuring unit 118 may be an angular velocity sensor or a geomagnetic sensor.

In FIG. 1A, the FPD 103 is disposed on the back of the subject 105 but. When the mobile radiography unit 101 is conveyed together with the FPD 103, the FPD 103 is housed in the FPD housing unit 110 and conveyed. When the user performs radiation imaging, the FPD 103 held in the FPD housing unit 110 is taken out to the back of the subject 105.

The details of the radiation generator 102 are shown in FIG. 1B. The radiation generator 102 includes a tube 115 and an aperture 116. In this embodiment, the second display 117 and the first orientation measuring unit 113 are mounted on the aperture 116. The first orientation measuring unit 113 of this embodiment is an acceleration sensor. The orientation measuring unit 118 may be an angular velocity sensor or a geomagnetic sensor.

The aperture 116 includes a mechanism (including a stepping motor) that operates in accordance with a command of a computer mounted in the casing 108 to change the size of the radiation field and the rotation angle of the FPD 103.

Examples of the first housing determination unit 112 and the second housing determination unit 114 are electrical connectors for the mobile radiography unit 101 and the FPD 103. These electrical connectors are disposed at the mobile radiography unit 101 to charge the FPD 103. In this embodiment, the electrical connectors are also used to determine that the FPD 103 is housed in the FPD housing unit 110 of the mobile radiography unit 101 when the connectors of the mobile radiography unit 101 and the FPD 103 are connected so that the FPD 103 is being charged.

In this embodiment, when the FPD 103 is housed, the mobile radiography unit 101 and the FPD 103 are electrically connected with the first housing determination unit 112 and the second housing determination unit 114. However, the first housing determination unit 112 and the second housing determination unit 114 of this embodiment are provided to indicate that the FPD 103 is at a specific position, and therefore do not necessarily have to be electrically connected.

For example, the functions of the first housing determination unit 112 and the second housing determination unit 114 may be achieved by a proximity determination unit, such as Bluetooth® or near-field communication (NFC).

Alternatively, a weight scale for measuring the weight of the FPD 103 may be mounted in the FPD housing unit 110 of the mobile radiography unit 101. This allows determination that the FPD 103 is housed when the value of the weight scale is approximately the same as the weight of the FPD 103.

In this case, if the imaging plane of the FPD 103 is rectangular, so that the orientation has to be determined, the orientation is determined using, for example, a gravity sensor mounted on the FPD 103. As another alternative, a camera is mounted at the mobile radiography unit 101, and when the camera recognizes the FPD 103, it is determined that the FPD 103 is housed.

The FPD 103 may be provided with a sensor for determining whether the FPD 103 is housed. For example, sensors that distinguish between light and dark may be provided at the four corners of the FPD 103. When specific two sensors detect light and the other two sensors detect dark, it can be determined that the FPD 103 is housed in the FPD housing unit 110. This also allows determination of the orientation of the housing. Furthermore, in the case of a configuration in which the second control unit 203 of the FPD 103 has the function of a setting unit 205, described later, the determination of mounting can be made only at the FPD 103, thereby facilitating implementation of the mobile radiography unit 101.

Figure 2:
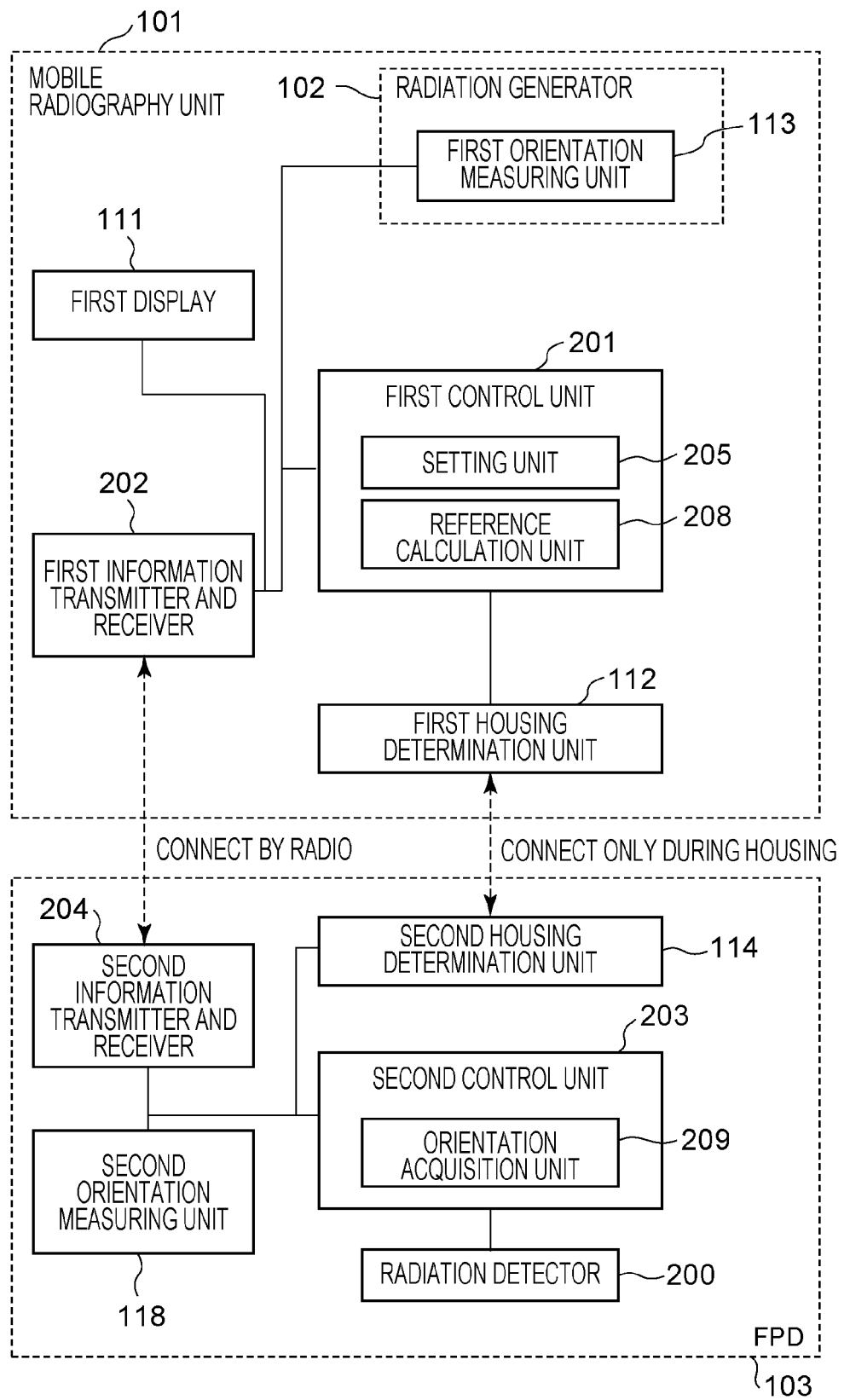
FIG. 2 is a diagram illustrating a mobile radiography unit and a flat panel detector (FPD) according the first embodiment.

Referring next to FIG. 2, a configuration example of the mobile radiography unit 101 and the FPD 103 in this embodiment will be described.

First, the components of the mobile radiography unit 101 will be described. The mobile radiography unit 101 houses a first control unit 201. The first control unit 201 may be a general-purpose computer constituted by hardware including a central processing unit (CPU), a main storage, such as a dynamic random-access memory (DRAM), and an auxiliary storage, such as a solid state drive (SSD) or a hard disk drive (HDD). The first control unit 201 has the functions of the setting unit 205 and a reference calculation unit 208, described later.

The first control unit 201 connects to the radiation generator 102 to control radiation, such as whether to emit radiation. The first control unit 201 connects to the first orientation measuring unit 113 to calculate the reference orientation of the radiation generator 102. The reference orientation of the radiation generator 102 can be calculated by the reference calculation unit 208 of the first control unit 201 from a value obtained by the first orientation measuring unit 113.

The first control unit 201 connects to the second orientation measuring unit 118 via the first information transmitter and receiver 202 and the second information transmitter and receiver 204 to calculate the reference orientation of the FPD 103. The reference orientation of the FPD 103 can be calculated by the reference calculation unit 208 of the first control unit 201 from the value of the second orientation measuring unit 118. The first control unit 201 determined the timing of setting the reference orientations of the radiation generator 102 and the FPD 103. This determination is made with the function of the setting unit 205 of the first control unit 201.

The reference orientation is a reference orientation at a certain time for calculating the orientation of the apparatus. In this embodiment, the radiation generator 102 and the FPD 103 each include an acceleration sensor for calculating the respective orientations.

To calculate the orientation using the acceleration sensor, accelerations obtained by the acceleration sensor are cumulated to calculate a velocity at a certain time and the velocities are cumulated again to be converted to displacement (position). However, what can be calculated with the above method is the sum of the orientation changes and therefore cannot be calculated accurately unless the reference orientation is known. The setting unit 205 determines appropriate timing to set the reference orientations of the radiation generator 102 and the FPD 103. This timing will be described later.

The first control unit 201 connects to the first information transmitter and receiver 202. Examples of the first information transmitter and receiver 202 include a wireless local area network (LAN) device, a Bluetooth device, and an ultra wide band (UWB) device. Transmission and reception of information to/from the FPD 103 can be performed by connecting to the second information transmitter and receiver 204 of the FPD 103 using the first information transmitter and receiver 202.

For example, in this embodiment, the setting unit 205 is mounted in the mobile radiography unit 101, so that information on the setting of the reference orientation is transmitted to the FPD 103 using the first information transmitter and receiver 202. The first information transmitter and receiver 202 also has the function of receiving orientation information obtained by the orientation acquisition unit 209 of the FPD 103. The second information transmitter and receiver 204 connects to the first information transmitter and receiver 202 by radio or the like to be used also for communicating with the mobile radiography unit 101 to change information on radiation control, such as whether to emit radiation, and transmitting images acquired by the FPD 103.

The first control unit 201 connects also to the first display 111 also serving as an input device, so that the user can input protocol information on radiation imaging via the first display 111. The first control unit 201 detects input of the protocol information.

In this embodiment, the FPD 103 includes the second control unit 203, the second information transmitter and receiver 204, the second orientation measuring unit 118, and the second housing determination unit 114. As shown in FIG. 2, these units are electrically connected to one another. The second control unit 203 can be constituted by a CPU, a main memory, and an auxiliary storage as is the first control unit 201.

The second control unit 203 may be simpler than the first control unit 201 of the mobile radiography unit 101 because the FPD 103 needs to be compact, lightweight, and power saving. To meet such requirement, the second control unit 203 of the FPD 103 may be a field programmable gate array (FPGA) or a dedicated integrated circuit (IC).

In this embodiment, the function of the orientation acquisition unit 209 is achieved by the second control unit 203. The orientation acquisition unit 209 calculates the orientation of the FPD 103 from the reference orientation calculated by the reference calculation unit 208 and set by the setting unit 205 and a value calculated by the second orientation measuring unit 118.

The relationship between an angle θ(t) and an angular velocity $\omega_\theta(t)$ about X-axis at time t, the relationship between a rotation angle $\omega_\varphi(t)$ and an angular velocity $\omega_\eta(t)$ about Y-axis at time t, and the relationship between a rotation angle η(t) and an angular velocity φ(t) about Z-axis at time t is expressed as:

$$\theta(t) = \theta(0) + \sum_{k=1}^{n} \omega_\theta(k\Delta t)\Delta t \quad \text{Exp. 1}$$

$$\varphi(t) = \varphi(0) + \sum_{k=1}^{n} \omega_\varphi(k\Delta t)\Delta t \quad \text{Exp. 2}$$

$$\eta(t) = \eta(0) + \sum_{k=1}^{n} \omega_\eta(k\Delta t)\Delta t \quad \text{Exp. 3}$$

where Δt, is the angular velocity measurement time interval, and n is the number of measurements (t=nΔt).

Using a gyroscope as the second orientation measuring unit 118 allows obtaining the value of an angular velocity in the coordinate system of the gyroscope. In calculating an angle from the angular velocity obtained by the gyroscope, the angular velocity in the coordinate system of the gyroscope is converted to an angle in a desired coordinate system. Known method may be used for this conversion.

The position is derived by calculating the sum of the accelerations to derive the velocity and then summing the velocities. Let x(t), $v_x(t)$, and $a_x(t)$ be X-axis components of position, velocity, an acceleration at time t, respectively, y(t), $v_y(t)$, and $a_y(t)$ be Y-axis components, and z(t), $v_z(t)$, and $a_z(t)$ be Z-axis components, respectively. The velocities $v_x(t)$, $v_y(t)$, and $v_z(t)$ at time t are expressed as:

$$v_x(t) = v_x(0) + \sum_{k=1}^{n} a_x(k\Delta t)\Delta t \quad \text{Exp. 4}$$

$$v_y(t) = v_y(0) + \sum_{k=1}^{n} a_y(k\Delta t)\Delta t \quad \text{Exp. 5}$$

$$v_z(t) = v_z(0) + \sum_{k=1}^{n} a_z(k\Delta t)\Delta t \quad \text{Exp. 6}$$

where Δt is the measurement time interval, and n is the number of measurements (t=nΔt) as is the angular velocities (t=nΔt).

Therefore, the positions x(t), y(t), and z(t) are expressed as:

$$x(t) = x(0) + \sum_{k=1}^{n} v_x(k\Delta t)\Delta t \quad \text{Exp. 7}$$

$$y(t) = y(0) + \sum_{k=1}^{n} v_y(k\Delta t)\Delta t \quad \text{Exp. 8}$$

-continued $$z(t) = z(0) + \sum_{k=1}^{n} v_z(k\Delta t)\Delta t \qquad \text{Exp. 9}$$

Exps. 1 to 9 may adopt a known numerical integration scheme, such as a trapezoid formula or Simpson's formula, to increase the accuracy of summing. In this case, the accelerations $a_x(t)$, $a_y(t)$, and $a_z(t)$ detected by the acceleration sensor contain a gravity component. For this reason, the direction of gravity exerted on the FPD 103 may be calculated using the angles $\theta(t)$, $\phi(t)$, and $\eta(t)$ obtained with the gyroscope, and the x, y, and z components of the gravitational acceleration may be subtracted from the accelerations.

Figure 3A:
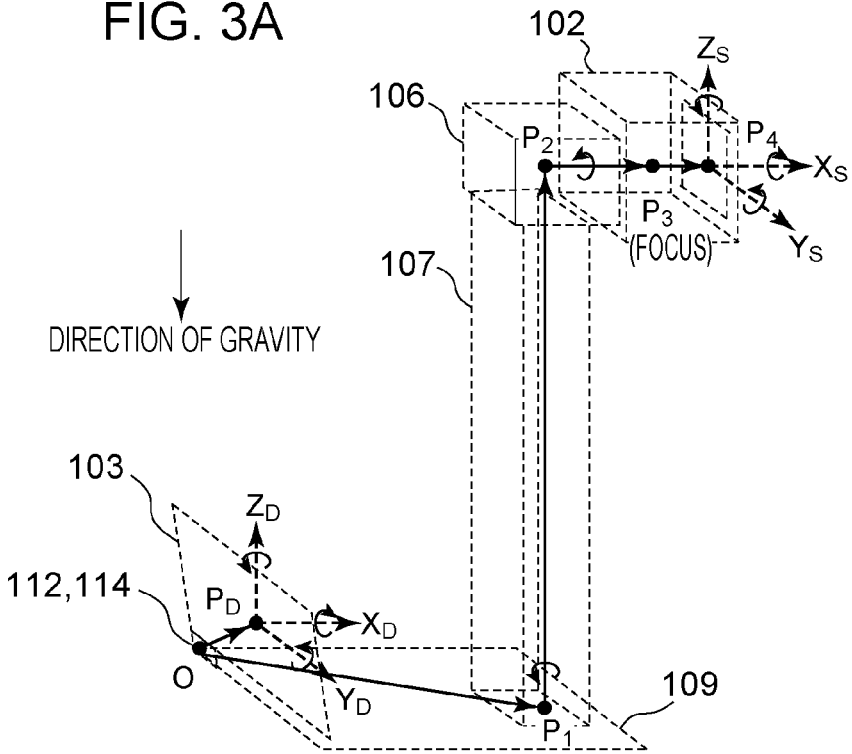
FIG. 3A is a diagram illustrating the relationship among the coordinates of the FPD and the coordinates of the radiation generator according to the first embodiment.
Figure 3B:
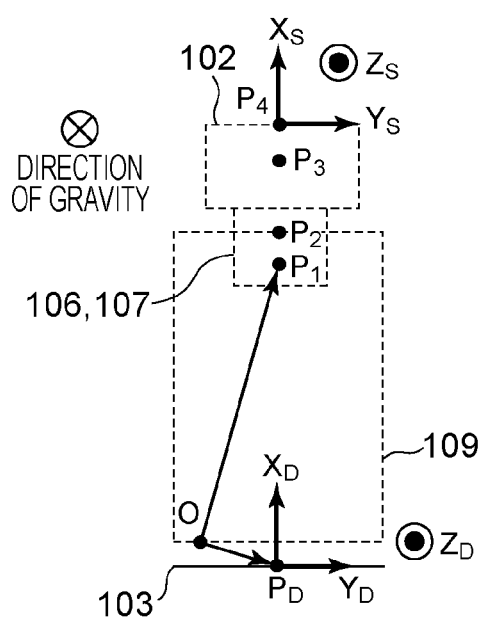
FIG. 3B is a diagram illustrating the relationship among the coordinates of the FPD and the coordinates of the radiation generator according to the first embodiment.
Figure 3C:
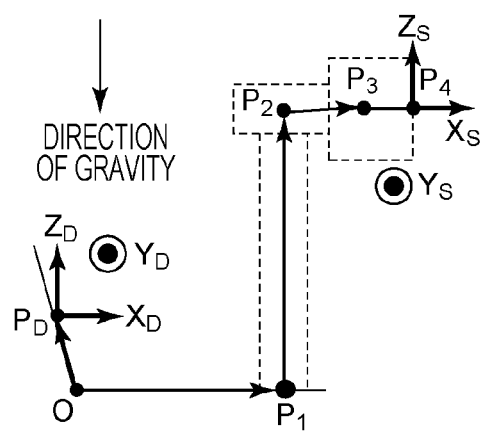
FIG. 3C is a diagram illustrating the relationship among the coordinates of the FPD and the coordinates of the radiation generator according to the first embodiment.

FIGS. 3A to 3C illustrate the relationship among the coordinates $X_D$, $Y_D$, and $Z_D$ of the FPD 103 and the coordinates $X_S$, $Y_S$, and $Z_S$ of the radiation generator 102 in this embodiment.

The coordinates of the FPD 103 and the coordinates of the radiation generator 102 are each defined as a coordinate relative to a reference point O. In this embodiment, the reference point O is defined as one point of a portion where the first housing determination unit 112 and the second housing determination unit 114 are connected. For example, one point of a portion where the first housing determination unit 112 and the second housing determination unit 114, for example, a corner or the center of gravity, is defined as the reference point O.

For the coordinates of the FPD 103, the axis parallel to and opposite to the gravity is set as the Z-axis, and an X-Y plane is set on the horizontal plane (a plane perpendicular to the direction in which gravity acts) with reference to the center $P_D$ of the FPD 103 (for example, the center of gravity). The y-direction is defined as being parallel to the base 109, and the x-direction is defined as be perpendicular to the y-direction (and in an X-Y plane).

For the coordinates of the radiation generator 102 as well, the axis parallel to and opposite to the gravity is set as the Z-axis, and an X-Y plane is set on the horizontal plane (a plane perpendicular to the direction in which gravity acts) with reference to the center $P_4$ of an emission surface. The y-direction is defined as being parallel to the base 109, and the x-direction is defined as being perpendicular to the y-direction. Calculation of the source image receptor distance (SID), which here refers to the distance to the incident surface of the FPD, uses the position $P_3$ of the focal point of the tube 115, instead of $P_4$.

The coordinates of the FPD 103 are expressed as vector $OP_D$, and the orientation of the FPD 103 is defined as rotation about the respective axes $X_D$, $Y_D$, and $Z_D$. If the FPD 103 is determined to be housed in the first housing determination unit 112 of the mobile radiography unit 101, the orientation of the FPD 103 is determined only from the geometric arrangement of the housed FPD 103 and the FPD housing unit 110.

In other word, when the FPD 103 is housed in the FPD housing unit 110 and is connected by the first housing determination unit 112 and the second housing determination unit 114, the vector $OP_D$ representing the orientation and the rotation angles about $X_D$, $Y_D$, and $Z_D$ take values that depend only on their respective outer shapes. The reference orientation of the FPD 103 may therefore be expressed by the vector $OP_D$ and the rotation angles about $X_D$, $Y_D$, and $Z_D$ when the FPD 103 is housed.

Similarly, the coordinates of the radiation generator are expressed as the vector $OP_4$. The vector $OP_4$ is expressed as the sum of four vectors, vector $OP_1$, vector $P_1P_2$, vector $P_2P_3$, and vector $P_3P_4$.

The vector OP' is a vector from the reference point O to one end of the second arm 107. The vector $P_1P_2$ is a vector from one end of the second arm 107 to the other end (in contact with the first arm 106) of the second arm 107. The vector $P_2P_3$ is a vector from one end of the first arm 106 to the focal point of the tube 115. The vector $P_3P_4$ is a vector from the focal point of the tube 115 to the center $P_4$ of a plane of the aperture from which radiation is emitted. The relationship is expressed as:

$$\overrightarrow{OP_4} = \overrightarrow{OP_1} + \overrightarrow{P_1P_2} + \overrightarrow{P_2P_3} + \overrightarrow{P_3P_4} \qquad \text{Exp. 10}$$

The coordinates of the focal point are expressed as:

$$\overrightarrow{OP_3} = \overrightarrow{OP_1} + \overrightarrow{P_1P_2} + \overrightarrow{P_2P_3} \qquad \text{Exp. 11}$$

The vector $OP_1$ is determined by the dimensions of the base 109. The vector $P_1P_2$ is determined by the length (the degree of extension/contraction) and the rotation of the second arm 107. The vector $P_2P_3$ is determined by the length (the degree of extension/contraction) and the rotation of the first arm 106. The vector $P_3P_4$ is fixed (depends on the position of the focal point of the tube 115 and the dimensions of the aperture 116).

In other words, in this embodiment, of the vector $OP_4$, amounts that change at the actual operation by the user are the length, the degree of extension/contraction, orientation, and rotation of the first arm 106, and the length, orientation, and rotation of the second arm 107. The initial state of the radiation generator 102 can be calculated from this information.

In transporting the mobile radiography unit 101, the first arm 106 and the second arm 107 are contracted as much as possible to facilitate transportation. In other words, the arms are in a specific state when the mobile radiography unit 101 is transported. This state is therefore be taken as the reference state of the arms.

Whether the arms are in the reference state can be determined using a known device. The orientation and rotation may be measured using potentiometers disposed at the individual contacts, for example. The extension/contraction of the arms can be measured using a range finder or the like. Alternatively, a mechanical or electrical switch that reacts only when the axes of the arms are in the reference state may be provided.

In this embodiment, the rotations of the radiation generator 102 about the coordinates $X_S$, $Y_S$, and $Z_S$ are calculated from the orientation of the first arm 106 and the orientation of the second arm 107. As described above, the rotation of the first arm 106 about the vector $P_2P_3$ can be controlled in addition to the direction and magnitude of the vector $P_2P_3$, and the rotation of the second arm 107 about the vector $P_1P_2$ can be controlled in addition to the direction and magnitude of the vector $P_1P_2$. Changing the directions and magnitudes of the arms allows the rotation about the $X_S$, $Y_S$, and $Z_S$ to be controlled.

Figure 4:
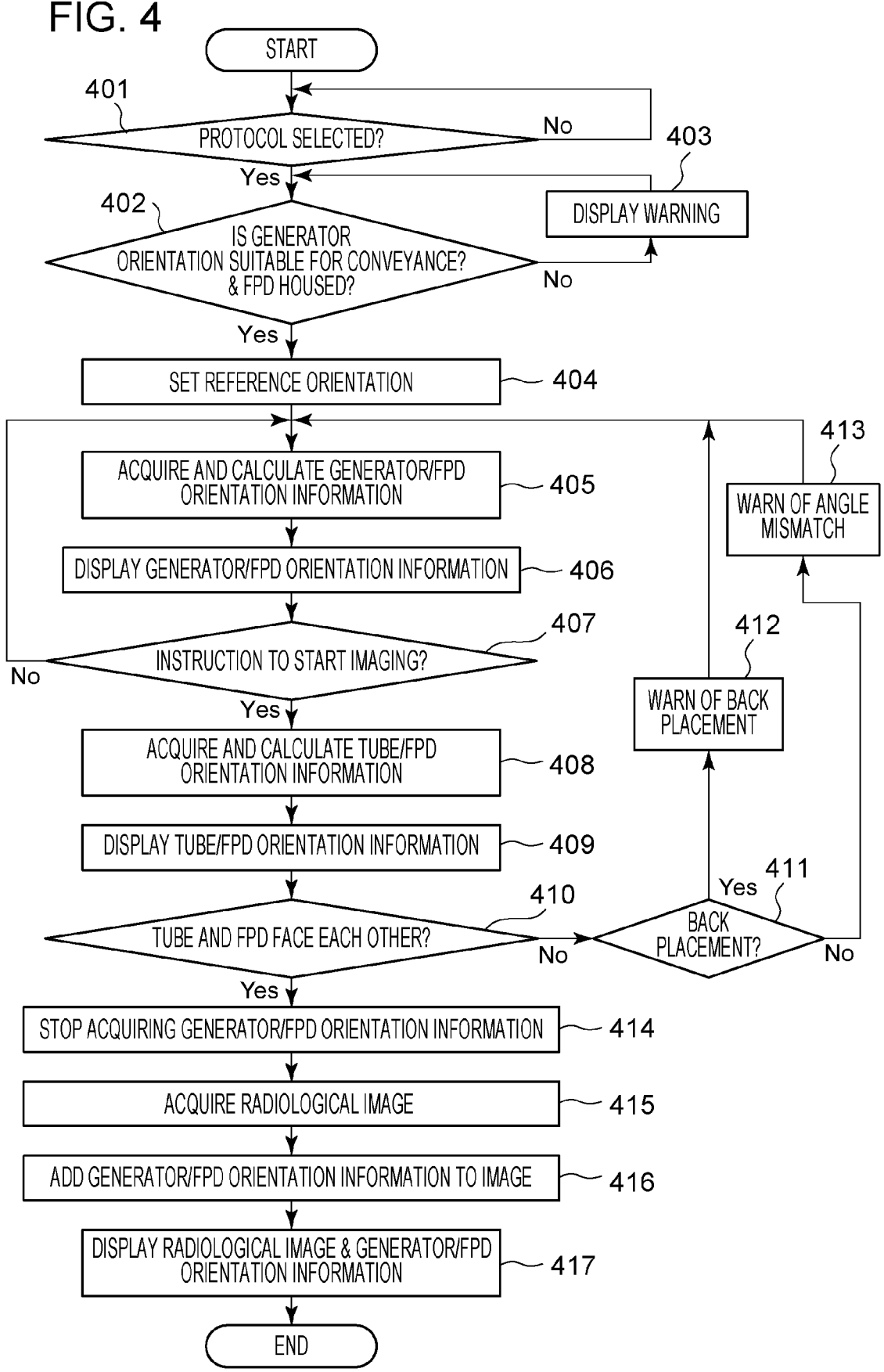
FIG. 4 is a flowchart for the processing of the radiation imaging apparatus according to the first embodiment.

FIG. 4 illustrates a processing procedure of the radiation imaging apparatus 100 in the first embodiment of the present invention. In step 401, the first control unit 201 determines whether a protocol for radiation imaging by the user has been selected via the first display 111.

Immediately after the protocol is selected, in step 402, the first control unit 201 mounted in the mobile radiography unit 101 determines whether the FPD 103 is housed. The first control unit 201 is connected to the first housing determination unit 112 of the mobile radiography unit in FIG. 2, so that the first control unit 201 can determine whether the FPD 103 is housed. If the FPD 103 is not properly housed, the reference orientation cannot be accurately calculated. For this reason, a warning is displayed in step 403, and then the determination whether the FPD 103 is housed is made again in step 402.

If in step 402 it is determined that the FPD 103 is properly housed, then in step 404 the first control unit 201 generates a trigger and, in response to the trigger, the setting unit 205 in the first control unit 201 sets a reference orientation. In step 402, it has been determined that the FPD 103 is at a specific position of the mobile radiography unit 101, and the radiation generator 102 is in an orientation suitable for transportation. For this reason, the reference orientation can be set in step 404.

In other words, the radiation imaging apparatus 100 of this embodiment can automatically set the reference orientation without a user's specific operation when protocol information for radiation imaging is set, and when the FPD 103 is precent at a specific position (in the FPD housing unit 110). After the protocol information is set, the user moves the first arm 106 and the second arm 107 but rarely moves the casing 108 and the base 109 to position the radiation generator 102.

In contrast, the FPD 103 does not move after the protocol information is set until the FPD 103 is drawn out of the FPD housing unit 110. For this reason, the period after the protocol information is set and while the FPD 103 is in the FPD housing unit 110 is the timing the reference orientation can be set.

In setting the reference orientation, considering both the timing in the imaging procedure and the position allows the reference orientation to be set more accurately. For example, if only the imaging procedure is taken into consideration, in other words, if the reference orientation is set at the selection of the protocol, the reference orientation changes according to the orientation of the FPD 103, so that the position and angle calculated at the later step depends on the reference orientation.

In contrast, in the case of a system in which the reference orientation is set by determining only the position, for example, whether the FPD housing unit 110 is present, the reference orientation can be set, for example, while the mobile radiography unit 101 is moving, which may decrease the accuracy of the position and angle.

Figure 5A:
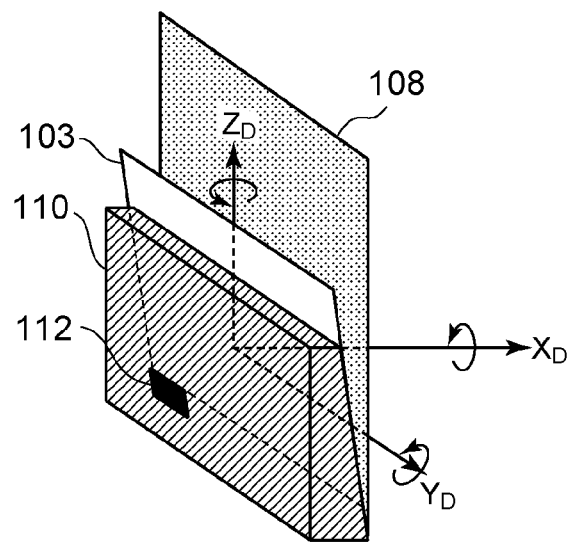
FIG. 5A is a diagram illustrating a method for initial setting according to the first embodiment.
Figure 5B:
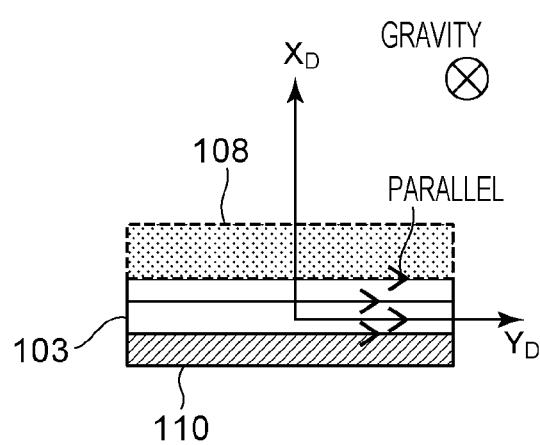
FIG. 5B is a diagram illustrating a method for initial setting according to the first embodiment.
Figure 5C:
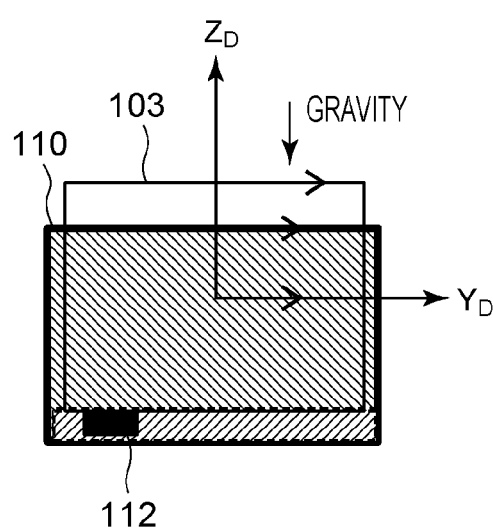
FIG. 5C is a diagram illustrating a method for initial setting according to the first embodiment.
Figure 5D:
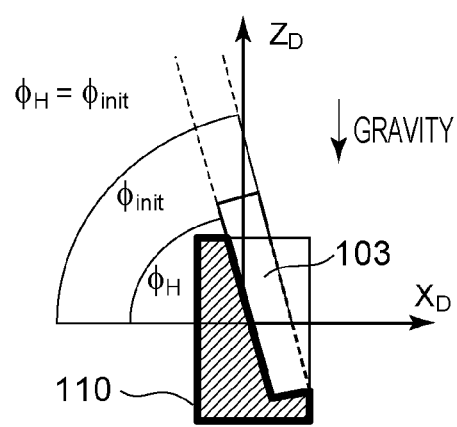
FIG. 5D is a diagram illustrating a method for initial setting according to the first embodiment.

FIGS. 5A to 5D FPD 103 illustrate a method of initial setting. FIG. 5A is a projection view of the FPD 103, one surface of the casing 108, the FPD housing unit 110, and the first housing determination unit 112, with the FPD 103 housed in the FPD housing unit 110, in this embodiment. FIGS. 5B, 5C, and 5D illustrate three surfaces in FIG. 5A.

In this embodiment, the FPD 103, the FPD housing unit 110, and one surface of the casing 108 are designed to be parallel with an axis $Y_D$ when the FPD 103 is housed. This design is illustrated in FIGS. 5B and 5C. Adopting such a design allows the angular relationship between the FPD 103 and the casing 108 in the initial state (housed state) to be determined. The respective rotation angles ($\eta D_{init}$ and $\theta D_{init}$) about Z-axis and X-axis are set to 0°.

As shown in FIG. 5D, one surface of the FPD housing unit 110 has an inclination of $\phi_H$. The inclination $\phi_H$ is less than 90°. This structure causes the FPD 103 and one surface of the FPD housing unit 110 to come into contact with each other under gravity, and, the FPD 103 to be parallel to the FPD housing unit 110 when housed. This causes one surface of the casing 108 to be parallel to the axis $Y_D$. Since the FPD 103 and the FPD housing unit 110 is in contact with each other in the initial state, the rotation angle $\phi D_{init}$ of the FPD 103 about the axis $Y_D$ in the initial state takes the same value as $\phi_H$.

In other words, in this embodiment, the respective rotation angles $\theta D_{init}$, $\phi D_{init}$, and $\eta D_{init}$ about the X-axis, the Y-axis, and the Z-axis in the initial state can be calculated from the dimensions of the mobile radiography unit 101.

For the rotation about the X-axis and the Y-axis of the three axial rotations, the relationship between the orientations and gravity can be calculated from the value from the acceleration sensor. According, the reference orientation may be set using the value from the acceleration sensor. However, only the axial rotation $\eta D_{init}$ about the Z-axis parallel to gravity cannot be obtained by the acceleration sensor, the reference orientation cannot be set from the value from the acceleration sensor. For this reason, providing a magnetic sensor serving as a detector and calculating an azimuth angle to a magnetic line generated by geomagnetism allows the reference orientation to be set.

The reference orientation of the FPD 103 can be calculated only from the dimensions of the mobile radiography unit 101 as described above. The reference orientation of the radiation generator 102 can be calculated from the orientations of the first arm 106 and the second arm 107 taken at transportation. Thus, using the dimensions of the mobile radiography unit 101 and the values determined from the information on the arms allows the reference orientations of the radiation generator 102 and the FPD 103 to be calculated and set.

In other words, in steps 401 to 404, the following processes are executed by the setting unit 205 of the radiation imaging apparatus 100.

The setting unit 205 sets at least one of the reference orientation of the FPD 103 (radiation detector) for calculating the orientation of the FPD 103 and the reference orientation of the radiation generator 102 for calculating the orientation of the radiation generator 102. This setting is performed by the setting unit 205 in response to detecting the mobile radiography unit 101 equipped with the radiation generator 102 has stood still, with the FPD 103 held. This is the processes executed in steps 401 to 404.

After the reference orientation is set in step 404, the orientation acquisition unit 209 starts to acquire and calculate the orientation information on the radiation generator 102 in step 405. The information to be calculated is the angles and the positions (SID) of the three components. The orientations of the radiation generator 102 and the FPD 103 can be determined from the reference orientations set in step 404 using Exps. 1 to 9.

The SID, if needed, can be expressed as:

$$|\overrightarrow{P_3P_D}| = |\overrightarrow{OP_D} - \overrightarrow{OP_3}| = \sqrt{(\overrightarrow{OP_D} - \overrightarrow{OP_3})_x^2 + (\overrightarrow{OP_D} - \overrightarrow{OP_3})_y^2 + (\overrightarrow{OP_D} - \overrightarrow{OP_3})_z^2} \quad \text{Exp. 12}$$

where $OP_D$ is the vector of the center of the FPD 103 seen from the origin, $OP_3$ is a vector of the focal point seen from the origin, $P_3P_D$ is a vector from the focal point to the center of the FPD 103, and SID is the length of the vector $P_3P_D$.

In Exp. 12, ( )$_x$ is the magnitude of x-component of the vector. The same applies to y-component and z-component.

Information on the calculated orientations of the radiation generator 102 and the FPD 103 is displayed in step 406, for example, on the first display 111 or the second display 117. For example, displaying the angle and the SID on the second display 117 of the radiation generator 102 allows the user to determine whether the current orientations are desired orientations during positioning of the subject.

Next, in step 407, it is determined whether an instruction to start imaging has been provided. This determination can be made by determining whether an exposure switch (not shown) provided at the mobile radiography unit 101 has been pressed. Step 405 and step 406 are repeated until an imaging start instruction is given, and the user adjusts the orientations so that the radiation field surface of the radiation generator 102 and the FPD 103 face each other while viewing the first display 111 or the second display 117. When desired orientations are achieved, the user presses the exposure switch to go to step 408.

If an imaging start instruction is given, then in step 408 the orientation acquisition unit 209 acquires can calculates information on the orientation of the radiation generator 102 immediately before radiation. In step 409, the orientation information is displayed on the first display 111 or the second display 117, and then in step 410 the orientation acquisition unit 209 determines the facing relationship between the radiation generator 102 and the FPD 103.

Figure 6A:
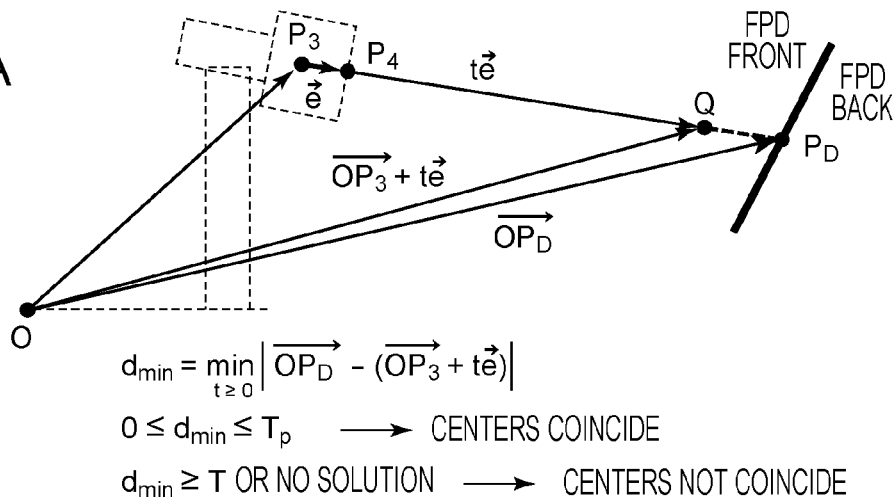
FIG. 6A is a diagram illustrating an example of a method for examining the arrangement of the radiation generator and the FPD according to the first embodiment.
Figure 6B:
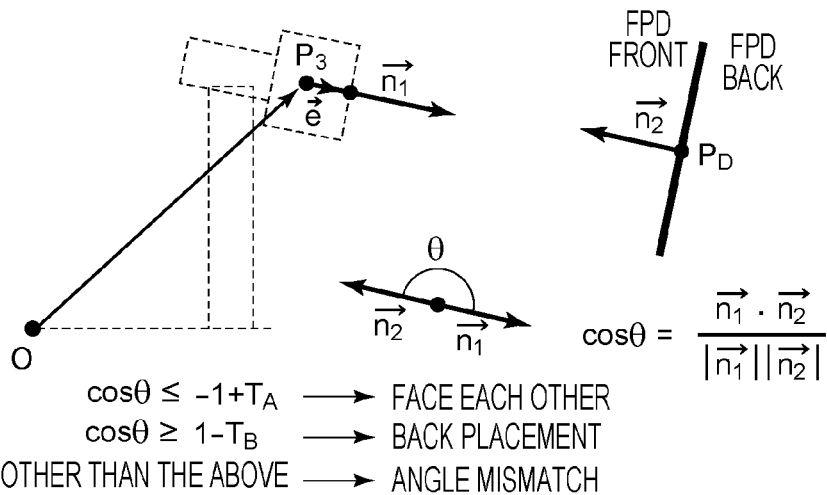
FIG. 6B is a diagram illustrating an example of a method for examining the arrangement of the radiation generator and the FPD according to the first embodiment.
Figure 6C:
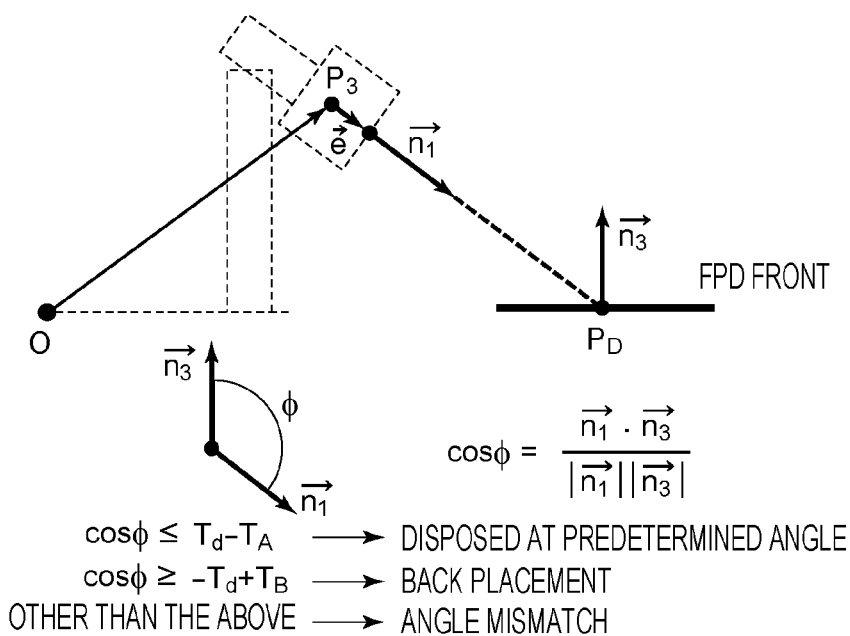
FIG. 6C is a diagram illustrating an example of a method for examining the arrangement of the radiation generator and the FPD according to the first embodiment.

FIGS. 6A to 6C illustrate an example of a method for determining the facing relationship between the radiation generator 102 and the FPD 103. To determine whether the radiation generator 102 and the FPD 103 face each other, the orientation acquisition unit 209 determines whether the center of the FPD 103 and the center of the radiation field coincide (FIG. 6A) and determines whether the radiation field surface and the incident surface of the FPD 103 are parallel to each other (FIG. 6B).

For FIG. 6A, the difference $d_{min}$ between the center of the FPD 103 and the center of the radiation field is expressed as:

$$d_{min} = \min_{t \geq 0} \left| \overrightarrow{OP_D} - (\overrightarrow{OP_3} + t\vec{e}) \right|$$

Exp. 13 where $OP_D$ is the vector of the position of the FPD 103, and vector $OP_3$+t×vector e (t is a positive constant and Q is the end point of vector e) is the center of the radiation field.

The determination can be made using Exp. 14 for a threshold $T_p$ of acceptable distances.

$$\begin{cases} \text{If } 0 \leq d_{min} \leq T_p \text{ the centers coincide} \\ \text{If } d_{min} \geq T_p \text{ or no solution, the centers do not coincide} \end{cases}$$

Exp. 14

FIG. 6A illustrates a method for determining whether the center of the FPD 103 and the center of the radiation field coincide.

In other words, whether the positions are proper can be determined by expressing the coordinate $P_D$ and the vector $P_3Q$ as an expression on three-dimensional coordinates, substituting the distance between the point $P_D$ and the half line $P_3Q$ into a known formula, and comparing the distance with the threshold $T_p$.

The vector e represents the direction in which the radiation from the tube travels. The vector e can be determined from information on the dimensions of the mobile radiography unit 101 and the current orientation of the radiation generator 102 (the current orientation is measured by the first orientation measuring unit 113). An example of the vector e can be the difference in position between the radiation generator 102 at position $P_3$ and the aperture 116 at position $P_4$.

For the determination of the arrangement of the radiation generator 102 and the FPD 103 in FIG. 6B, the angle φ between a normal vector $n_1$ that aligns with the direction of radiation from the radiation generator 102 and a normal vector $n_3$ perpendicular to the detection surface of the FPD 103 is determined, and the value cos θ is calculated using Exp. 15.

$$\cos\theta = \frac{\vec{n_1} \cdot \vec{n_2}}{|\vec{n_1}||\vec{n_2}|}$$

Exp. 15 where • represents the inner product of the two vectors), and the value cos θ is used for the determination as in Exp. 16.

$$\begin{cases} \text{If } \cos\theta \leq -1 + T_A, \text{ the radiation generator and the} \\ \quad FPD \text{ face each other} \\ \text{If } \cos\theta \geq 1 - T_B, \text{ the } PFD \text{ faces on the back} \\ \text{If other than the above, the radiation generator and} \\ \quad \text{the } FPD \text{ are not parallel to each other} \end{cases}$$

Exp. 16 where $T_A$ and $T_B$ are thresholds representing the tolerance of the angles.

Depending on the imaging procedure, radiation may be applied at an angle. FIG. 6C illustrates a case in which radiation is applied at an angle to the FPD 103. For the determination of the arrangement of the radiation generator 102 and the FPD 103 as in FIG. 6B, the angle φ between the normal vector $n_1$ that aligns with the direction of radiation from the radiation generator 102 and the normal vector $n_3$ perpendicular to the detection surface of the FPD 103 is determined, and the value cos θ is calculated using Exp. 17.

$$\cos\phi = \frac{\vec{n_1} \cdot \vec{n_3}}{|\vec{n_1}||\vec{n_3}|}$$

Exp. 17 where • represents the inner product of the two vectors, and the value cos θ is used for the determination as in Exp. 18.

$$\begin{cases} \text{If } \cos\phi \leq T_d - T_A, \text{ the radiation generator and the} \\ \quad FPD \text{ are arranged at a predetermined angle} \\ \text{If } \cos\phi \geq -T_d + T_B, \text{ the } FPD \text{ faces on the back} \\ \text{If other than the above, the radiation generator and} \\ \quad \text{the } FPD \text{ are not arranged at the same angle} \end{cases}$$

Exp. 18 where $T_d$ is the inner product of the normal vectors that are set according to the imaging procedure, and $T_A$ and $T_B$ are thresholds representing the tolerance of the angles.

FIGS. 6B and 6C illustrate a method for determining the arrangement of the radiation field surface of the radiation generator 102 and the incident surface of the FPD, in which the incident angles of the radiation incident on the FPD 103 differ.

The three angles (angles about axes $X_S$, $Y_S$, and $Z_S$ of the radiation generator 102 and the three angles (angles about axes $X_D$, $Y_D$, and $Z_D$) of the FPD 103 are calculated, and the angles are compared, respectively. This allows determining whether the radiation field surface of radiation from the radiation generator 102 and the incident surface of the FPD 103 are arranged according to the imaging procedure.

The orientations of the radiation generator 102 and the FPD 103 are calculated and obtained by the orientation acquisition unit 209 on the basis of the values obtained by the first orientation measuring unit 113 and the second orientation measuring unit 118, respectively. The normal vectors of the radiation generator 102 and the FPD 103 can be calculated by calculating the normal vectors of the two surfaces in the reference orientations before rotation and then rotating the normal vectors on the basis of angles obtained from the various sensors. The vector e used in FIG. 6A may also be used as the normal vector $n_1$ of the radiation generator 102. A known rotation matrix format may be used in calculating a normal vector after rotation.

Thus, in this embodiment, the orientation acquisition unit 209 acquires the relative relationship between the orientations of the radiation generator 102 and the FPD 103. If the orientation acquisition unit 209 determines that the centers of the radiation generator 102 and the FPD 103 coincide and the angle between them is within a predetermined range, then the orientation acquisition unit 209 determines whether the radiation generator 102 and the FPD 103 are arranged according to the imaging procedure.

Although the relative relationship between the orientations of the radiation generator 102 and the FPD 103 is obtained by the orientation acquisition unit 209 from the values from the first orientation measuring unit 113 and the second orientation measuring unit 118, this is illustrative only. For example, the orientation of the radiation generator 102 may be estimated from the positions of the first arm 106 and the second arm 107, not be calculated from the value from the first orientation measuring unit 113.

Using at least one of six components, the three components of the position about the three axes and the three components of the angle about the three axes, allows simple determination of facing. For determination of facing only using the angle of rotation about two axes other than rotation about an axis parallel to gravity, for example, only the angles calculated from values obtained by the acceleration sensor may be used. For determination using three-axes rotation, rotation about an axis parallel to gravity calculated from values obtained from an orientation sensor (a magnetic sensor) may be used. Determination of distance may be made using values obtained from a Bluetooth wireless device, for example.

FIG. 4 will be described again hereinbelow. If in step 410 it is determined that the centers of the radiation generator 102 and the FPD 103 do not coincide, or the radiation generator 102 and the FPD 103 are not arranged in a predetermined state, the radiation generator 102 does not emit radiation to the FPD 103, and the process goes to step 411.

In step 411, it is determined whether the FPD 103 is in back placement, and a waning of back placement is displayed in step 412 or a warning of angle mismatch is displayed in step 413. Separating warnings for center not coincide and placement mismatch (angle mismatch or back placement) allows the user to be given a hint for repositioning.

While this embodiment is configured not to permit radiation, radiation may be permitted, with only a warning displayed. Radiation may be permitted when the button is pressed for a given time, or when the button is pressed again after a warning is displayed.

If the radiation generator 102 and the FPD 103 face each other, then in step 414 acquisition of information on the orientations of the radiation generator 102 and the FPD 103 ends. Next, in step 415, the FPD 103 generates an image based on the radiation emitted from the radiation generator 102.

In step 416, information on the orientations of the radiation generator 102 and the FPD 103 is added to the image. The addition of orientation information to the image can be performed by, for example, the first control unit 201 in the mobile radiography unit 101. Examples of a method of addition include common methods, such as addition to the header of the image, embedding into the image itself (for example, decreasing the pixel values of the image area allows embedding of numerical values of orientations into the image), and generation of a dedicated file in which orientation information is recorded. Examples of the orientation information added include the angles and the SIDs of the radiation generator 102 and the FPD 103.

In step 417, the acquired and added orientation information is displayed on the first display 111 and the second display 117. This allows the user to determine whether imaging has succeeded and, if failed (imaging failure), to examine the causes of the failure from the acquired radiological image and the orientation information displayed on the first display 111 of the mobile radiography unit 101.

In this embodiment, the second orientation measuring unit 118 does not necessarily have to be the acceleration sensor, the geomagnetism sensor, or the angular velocity, but can also be any device that measures the rotation and extension/contraction of the first arm 106 and the second arm 107 and the rotation of the aperture 116.

For example, a mechanism to control rotation and expansion/contraction can be constituted by a known electrical component, a step motor, and the first control unit 201 of the mobile radiography unit 101. This allows calculation of the orientations using parameters (orientation control parameters) for use in the control mechanism, instead of calculation of the orientations based on the values measured by the sensor. The orientation control parameters may be back-calculated from the conditions of the mechanism (orientations and the state of motion).

In this embodiment, the distances are derived using an acceleration sensor, but a wireless LAN device, a Bluetooth device, or a UWB device may be used, as described above. As an alternative, a magnetic sensor may be used to derive the distances, in which a magnetic field is artificially generated to identify the position. Aa further alternative, an acceleration sensor, a wireless LAN device, a Bluetooth device, a UWB device, and a magnetic sensor may be combined to further improve the distance measurement accuracy.

Similarly for the angles, by combining angles obtained from a gravity sensor, angles calculated from angular velocities, and azimuth angles calculated from geomagnetism, the measurement accuracy can be further enhanced.

In this embodiment, the reference orientations are set at the selection of a protocol. The reference orientation may be set at the timing when the device for which the reference orientation is to be set stands still on certain coordinates fixed on the ground.

For example, if the mobile radiography unit 101 is moving, the radiation generator 102 and the FPD 103 move together with the mobile radiography unit 101, so that the radiation generator 102 and the FPD 103 move with respect to certain coordinates fixed on the ground. Similarly, in positioning the radiation generator 102 or the FPD 103, the radiation generator 102 or the FPD 103 moves with respect to certain coordinates fixed on the ground.

In a general imaging procedure, the period in which the FPD 103 stands still with respect to certain coordinates fixed on the ground is during the period from when the mobile radiography unit 101 is moved near the subject 105 until the FPD 103 is moved to start positioning of the FPD 103. For this reason, by detecting the processes performed during this period of the processing procedure, the reference orientation can be set, with the FPD 103 standing still with respect to certain coordinates fixed on the ground.

Similarly, the period in which the radiation generator 102 stands still with respect to certain coordinates fixed on the ground is during the period from when the mobile radiography unit 101 is moved near the subject 105 until the radiation generator 102 is moved to start positioning of the radiation generator 102. For this reason, by detecting the processes performed during this period of the processing procedure, the reference orientation can be set, with the radiation generator 102 standing still with respect to certain coordinates fixed on the ground.

An example of a specific timing for setting the reference orientations is the instant when the FPD 103 or the radiation generator 102 comes into operation for positioning. In this embodiment, the mobile radiography unit 101 and the FPD 103 include the first housing determination unit 112 and the second housing determination unit 114, respectively, to be connected by the electrical connectors, as described above. At the start of the positioning of the FPD 103, the first housing determination unit 112 and the second housing determination unit 114 is disconnected, and the first control unit 201 detects the disconnection and can set the reference orientation.

Similarly for the radiation generator 102, by disposing electrical components for detecting the motion of the arms, such as potentiometers, and detecting the start of rotation with the first control unit 201, the reference orientation can be set.

In detecting the start of positioning and setting the reference orientations, the FPD 103 or the radiation generator 102 has already started to move when the setting unit 205 detects a trigger and sets the reference orientations. This causes a slight gap from the standstill on certain coordinates on the ground.

For this reason, the setting unit 205 may hold the output values from the first orientation measuring unit 113 and the second orientation measuring unit 118 for a given length of time. In other words, the output values from the first orientation measuring unit 113 and the second orientation measuring unit 118 immediately before the reference orientations are set are held to use in setting the reference orientations.

The period of time to hold the output may be determined by measuring the time from detection of the start of positioning to setting the reference orientations in advance. In one example, the hold time is about 500 milliseconds.

Another example of the timing of setting the reference orientations is the timing when the standstill of the mobile radiography unit 101 is detected. The standstill of the mobile radiography unit 101 is detected, for example, using a method of detecting the rotation speed of the wheels of the mobile radiography unit 101 or using a position detecting sensor, such as an acceleration sensor or a global positioning system (GPS) sensor, mounted in the mobile radiography unit 101.

For example, when the rotation speed of the wheels or the output values from the sensor becomes a threshold or less, the first control unit 201 determines that the mobile radiography unit 101 has come to rest. After a certain period of time (for example, 1 second) after the first control unit 201 determines that the mobile radiography unit 101 has come to a standstill, the first control unit 201 generates a trigger and, in response to receiving the trigger, the setting unit 205 sets the reference orientations.

If the mobile radiography unit 101 includes a brake or a locking mechanism, the first control unit 201 may detect whether the mobile radiography unit 101 is at a stop in response to a signal to detect that the brake or the locking mechanism is working for a predetermined period of time.

Figure 7:
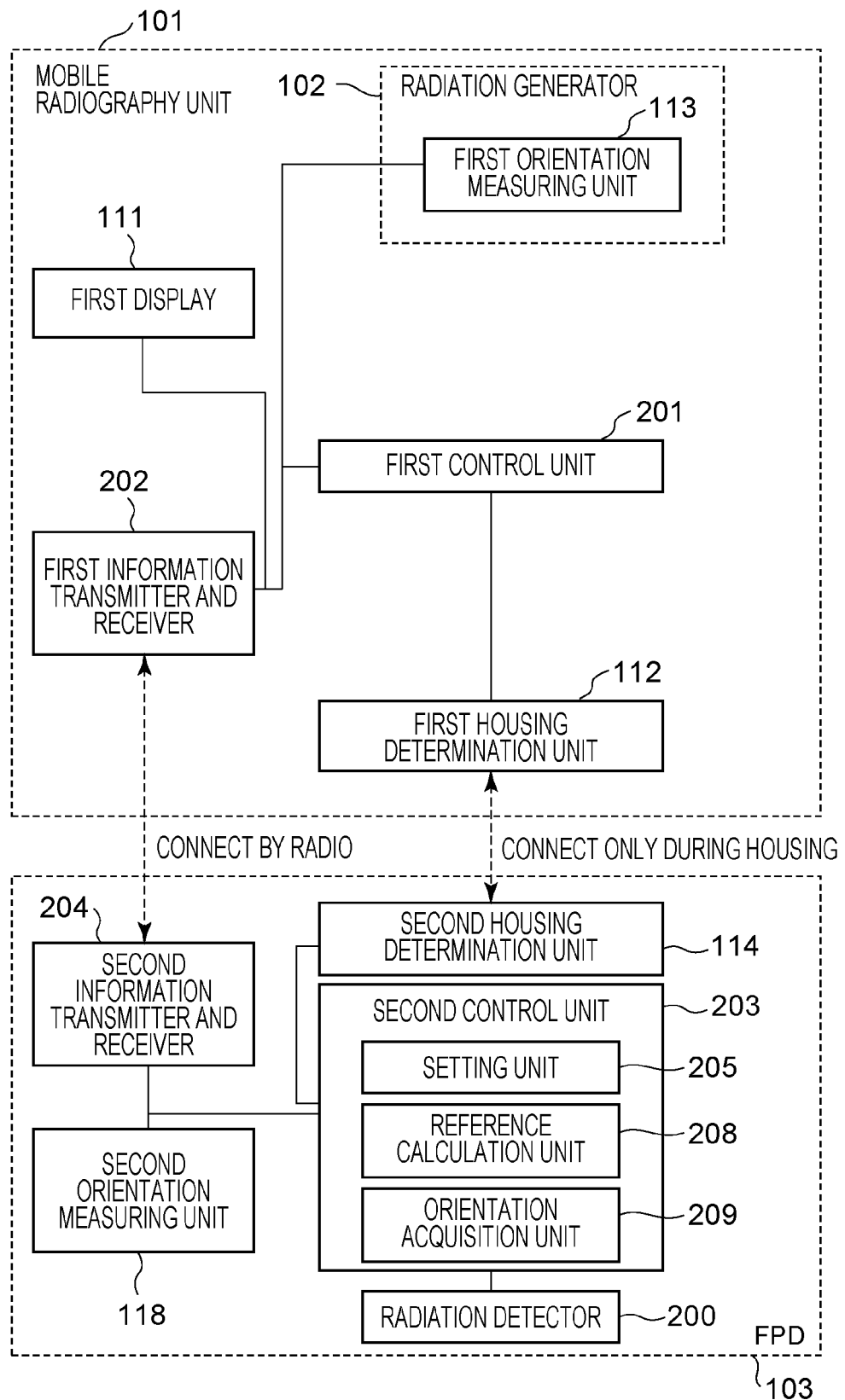
FIG. 7 is a diagram illustrating a mobile radiography unit and an FPD according a modification.

In this embodiment, the functions of the setting unit 205 and the reference calculation unit 208 are held by the first control unit 201 of the mobile radiography unit 101, and the function of the orientation acquisition unit 209 is held by the second control unit 203 of the FPD 103, but this is illustrative only. In one modification, the functions of the setting unit 205 and the reference calculation unit 208 may be held by the second control unit 203 of the FPD 103, as shown in FIG. 7. Similarly, the function of the orientation acquisition unit 209 may be held by the first control unit 201 of the mobile radiography unit 101.

Second Embodiment

In the first embodiment, it is assumed that the mobile radiography unit 101 does not move after the initial state is determined. In a second embodiment, it is assumed that a mobile radiography unit 701 moves after the initial state is determined.

Figure 8:
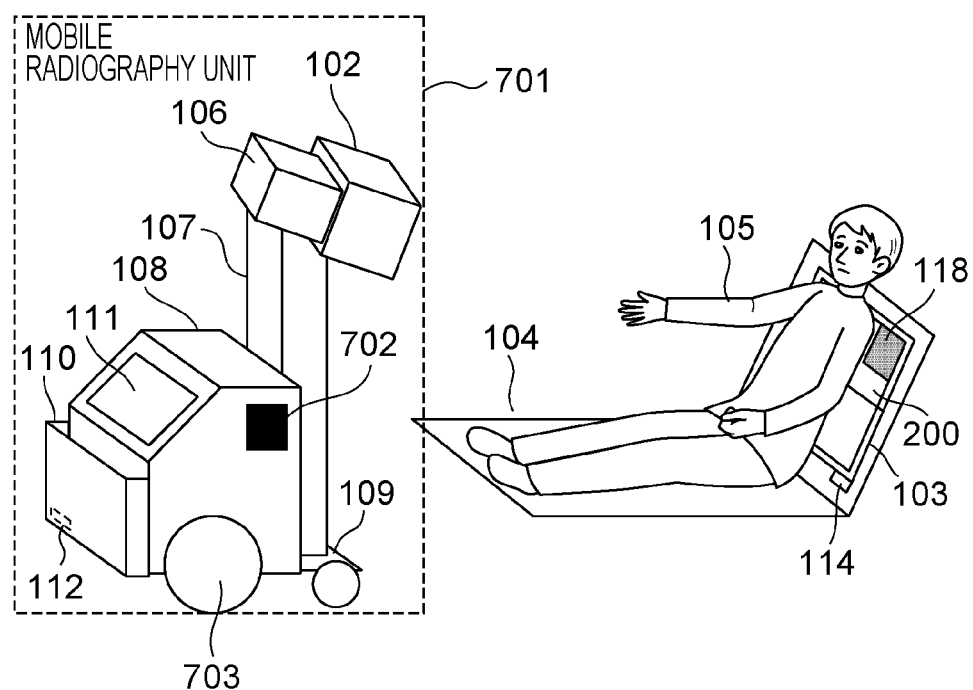
FIG. 8 is a diagram illustrating a configuration example of a radiation imaging apparatus according to a second embodiment.

FIG. 8 illustrates a configuration example of this embodiment. The configuration of this embodiment is similar to the configuration of the first embodiment except that a sensor 702, which is a movement measuring unit for the mobile radiography unit 701, is mounted on the casing 108 of the mobile radiography unit 701.

In this embodiment, an acceleration sensor serving as a movement measuring unit is mounted on the casing 108. Instead, the movement measuring unit may have another configuration. For example, the sensor 702 may be a gyroscope or a magnetic sensor, not the acceleration sensor. The wheels 703 of the mobile radiography unit 701 often connect to a motor that supplies auxiliary power. Detecting the rotation of the motor allows detecting the rotation of the wheels 703 and determining whether the mobile radiography unit 701 is moving. In another example, a camera or an ultrasonic device may be mounted in the mobile radiography unit 701 to detect the motion.

Figure 9:
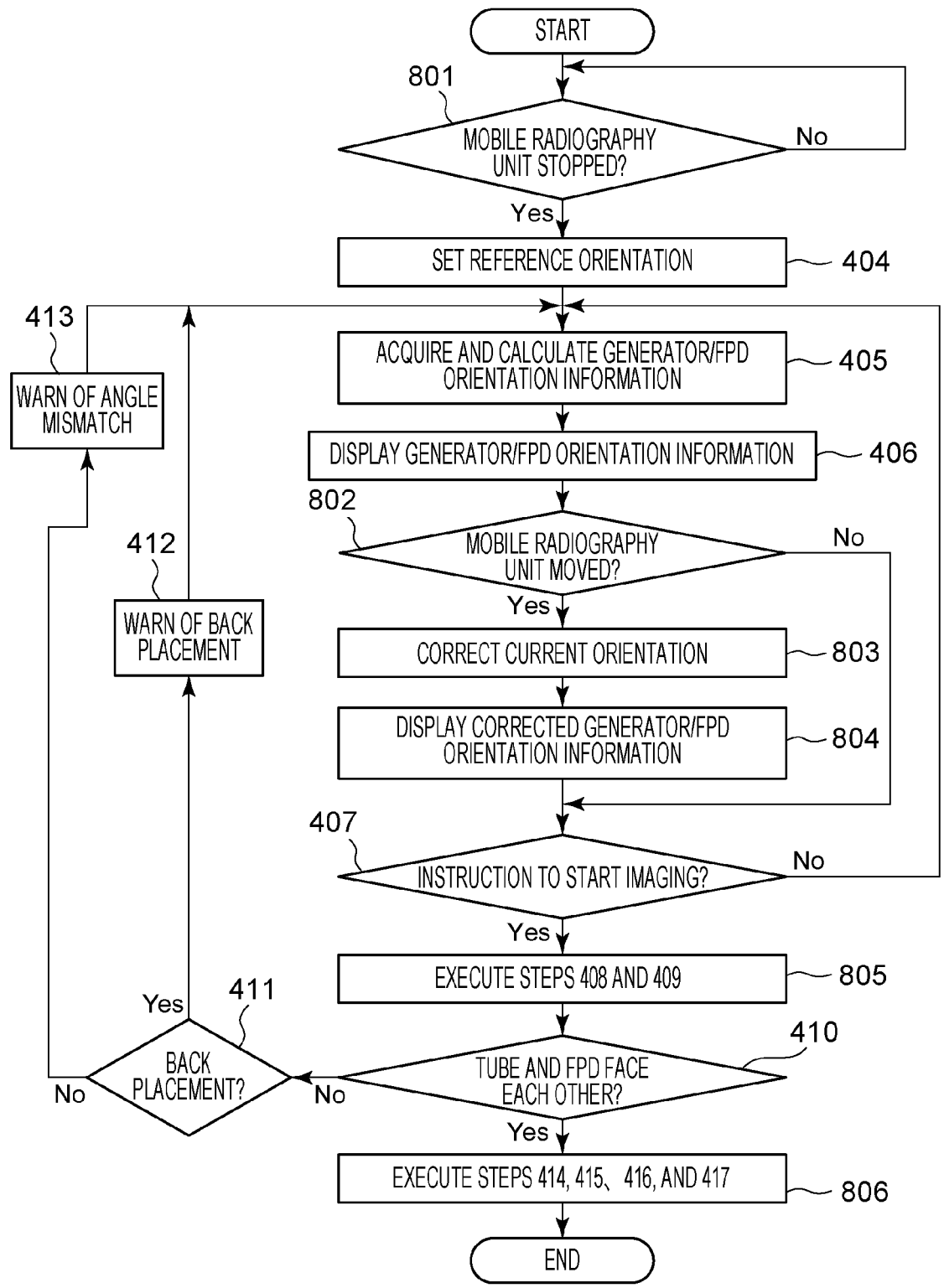
FIG. 9 is a flowchart for the processing of the radiation imaging apparatus according to the second embodiment.

FIG. 9 is a flowchart of this embodiment. The difference from the first embodiment is that determination of whether the mobile radiography unit 701 stands still or is moving and, if moving, the amount of movement using the sensor 702.

The setting of the reference orientation in step 404 is performed only when the mobile radiography unit 701 is determined to stand still in step 801. Whether the mobile radiography unit 701 stands still can be determined, for example, from the value of an acceleration obtained by the sensor 702. If it is assumed that there is no uniform motion, then it can be determined whether the mobile radiography unit 701 stands still only from the magnitude of the acceleration and the angular velocity.

Furthermore, assuming that only the angular velocity does not change (in the case where the mobile radiography unit 701 does not rotate about the sensor 702), the motion can be determined solely with the magnitude of the acceleration. A magnetic sensor may be used to examine the change in position, or a combination of an acceleration sensor, a gyroscope, a magnetic sensor, and another sensor may be used to determine whether the mobile radiography unit 701 stands still.

Steps 405 and 406 are the same as those of the first embodiment.

In step 802, it is determined whether the mobile radiography unit 701 moved between step 801 and 802. This determination can also be made using the sensor 702.

If in step 802 it is determined that the mobile radiography unit 701 moved, then in step 803 the reference orientation is corrected or reset based on the measured amount of movement. The reference orientation is corrected by calculating the sum (integration) of the accelerations, velocities, and angular velocities to calculate the displacement (the amount of change in position) and the angles and adding the values to the reference orientation set in step 404. Alternatively, the reference orientation may be reset by performing the setting of the reference orientation in step 404 again, without using the values set in step 404, to overwrite the reference orientation.

In step 804, the reset information on the orientations of the radiation generator 102 and the FPD 103 is displayed on the first display 111 or the second display 117. Subsequent steps are the same as the steps of the first embodiment.

In this embodiment, when the movement of the mobile radiography unit 701 is detected after the reference orientation is set, the reference orientation is reset based on the calculated amount of movement, but this is illustrative only. For example, a warning message that the mobile radiography unit 701 has moved or a warning message about the reset of the reference orientation may be displayed on the first display 111 or the second display 117 to warn the user.

Specifically, when the movement of the mobile radiography unit 701 is detected after the reference orientation is set, the distance of the movement or numerical information on the coordinates may be displayed as a warning message. Furthermore, a message "Mobile radiography unit moved after reference orientation is set", "Currently unable to calculate accurate orientation", or "Return the FPD to holder and then take it out" may be displayed. In this case, the user resets the reference orientation by returning the FPD 103 to the FPD housing unit 110 once and then drawing out the FPD 103 again. After the reset of the reference orientation is completed by a user's operation, a message such as "Reference orientation has been reset" may be displayed.

A warning message may be displayed while the reference orientation is being reset. In this case, until the reset of the reference orientation is completed, moving distance or numerical information on the coordinates may be displayed as a warning message. Alternatively, a message "Mobile radiography unit moved after reference orientation is set", "Currently unable to calculate accurate orientation", or "Resetting reference orientation" is displayed. After the reset of the reference orientation is completed, a message "Reference orientation has been reset" may be displayed.

Third Embodiment

In the first and second embodiments, the orientation information on the radiation generator 102 and the FPD 103 are used only for displaying their respective orientations or determination whether to emit radiation. In this embodiment, the radiation generator 102, the first arm 106, and the second arm 107 are equipped with a stepping motor (an example of a movable apparatus) at their movable portions. This allows the mobile radiography unit 101 to set the radiation generator 102 in a desired orientation without user intervention.

The mobile radiography unit 101 of this embodiment is the mobile radiography unit 101 of the first embodiment in which a stepping motor (not shown) is mounted. The first display 111 or the second display 117 also serving as a touch panel are provided with an automatic positioning button. The automatic positioning button may be provided separately from the display. In this embodiment, the mobile radiography unit 101 of the first embodiment is equipped with the stepping motor and the automatic positioning button.

Figure 10:
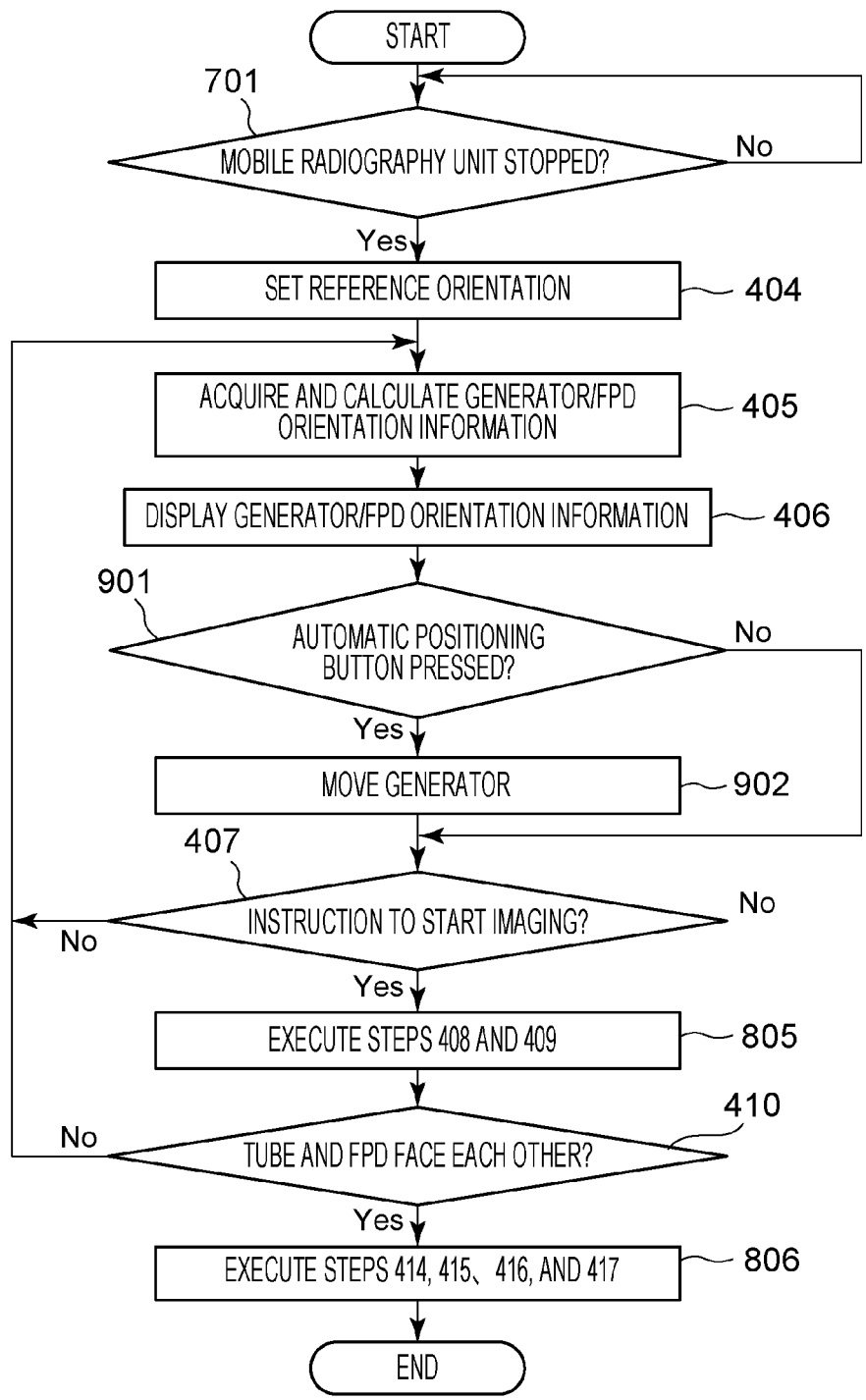
FIG. 10 is a flowchart for the processing of a radiation imaging apparatus according to a third embodiment.

FIG. 10 is a flowchart for the processing of the third embodiment. Steps 701, 404, 405, and 406 are the same as step 801, 404, 405, and 406 of the second embodiment.

In step 901, the mobile radiography unit 101 determines whether the automatic positioning button has been pressed. If yes, then in step 902 the radiation generator 102 is moved.

Figure 11A:
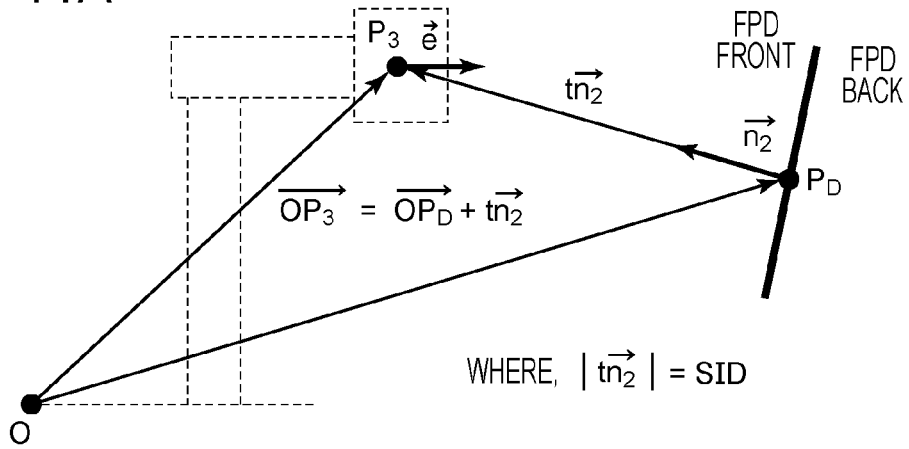
FIG. 11A is a diagram illustrating the details of a method for moving a radiation generator according to the third embodiment.
Figure 11B:
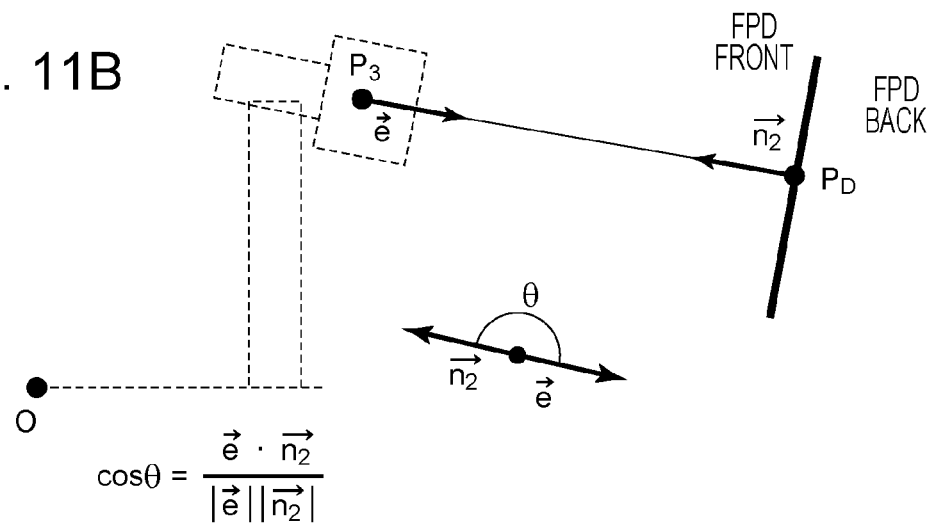
FIG. 11B is a diagram illustrating the details of a method for moving the radiation generator according to the third embodiment.
Figure 11C:
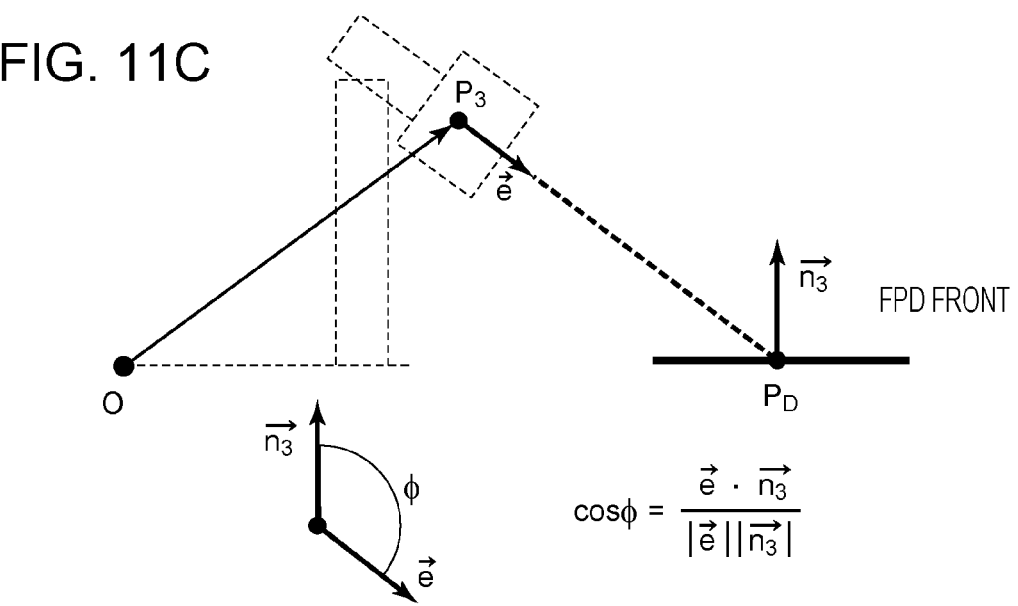
FIG. 11C is a diagram illustrating the details of a method for moving the radiation generator according to the third embodiment.

FIGS. 11A to 11C illustrate the details of a method for moving the radiation generator 102. The case where the orientation of the radiation generator 102 is determined so that the FPD 103 and the radiation generator 102 face each other will be described.

To check the facing, it is determined whether the center of the FPD 103 and the center of the radiation field surface irradiated with the radiation generator 102 coincide and whether the radiation field surface and the incident surface of the FPD 103 are arranged according to the imaging procedure. Accordingly, the two determinations are needed also for automatic positioning. The procedure for automatic positioning is shown in FIGS. 11A to 11C.

Alignment of the center of the FPD 103 and the center of the radiation field will be described with reference to FIG. 11A.

To align the center of the radiation field surface and the center of the incident surface, the radiation generator 102 is moved so that the position indicated by the sum of the vector $OP_D$ representing the position of the FPD 103 and a vector obtained by multiplying the normal vector of the FPD 103 by a positive real number coincide with the center of the radiation field or the focal point of the tube.

These vectors can be calculated from the values obtained from an acceleration sensor, a gyroscope, or a wireless connection device built in the FPD 103 (see the first embodiment). Accordingly, a variable required to determine the position of the radiation generator 102 is only a positive real number for the normal vector $n_2$. The positive real number is set based on the tube-focal-point distance (SID). Since the SID varies from imaging to imaging, the SID should be user configurable, or typical conditions for each procedure may be held in advance.

Even if the SID is unknown, the centers can be aligned. In this case, the direction and magnitude of the movement are expressed as a vector from the focal point to a point on a straight line represented by $OP_D + t \times n_2$ (t is a real number). The vector is perpendicular to the normal vector $n_2$.

To arrange the radiation field surface and the incident surface of the FPD 103 parallel in FIG. 11B, the orientation of the radiation generator 102 is changed so that the angle θ formed between the vector e indicating the radiation direction and the normal vector $n_2$ of the FPD 103 becomes approximately 180°. In other words, the position is determined so that Exp. 15 reaches approximately −1.

FIG. 11C illustrate an imaging procedure for setting the irradiation surface and the incident surface of the FPD 103 at an angle. In this case, the orientation of the radiation generator 102 is changed so that the angle φ formed between the vector e indicating the radiation direction and the normal vector $n_3$ of the FPD 103 reaches a predetermined angle determined by the imaging procedure. In other words, the position is determined so that Exp. 17 reaches approximately $T_d$.

The vector e varies according to the orientation of the radiation generator 102. In other words, the vector e can be varied using the stepping motors mounted in the first arm 106, the second arm 107, and the radiation generator 102.

If the automatic positioning button has not been pressed, then in step 407 it is determined whether to start imaging. The subsequent procedure is the same as in the second embodiment.

Fourth Embodiment

In this embodiment, not a mobile radiography unit, but an unmovable floor-mounted apparatus (an apparatus in which one of the radiation generator 102, the first arm 106, and the second arm 107 is fixed to a ceiling or a floor) will be described.

Figure 12:
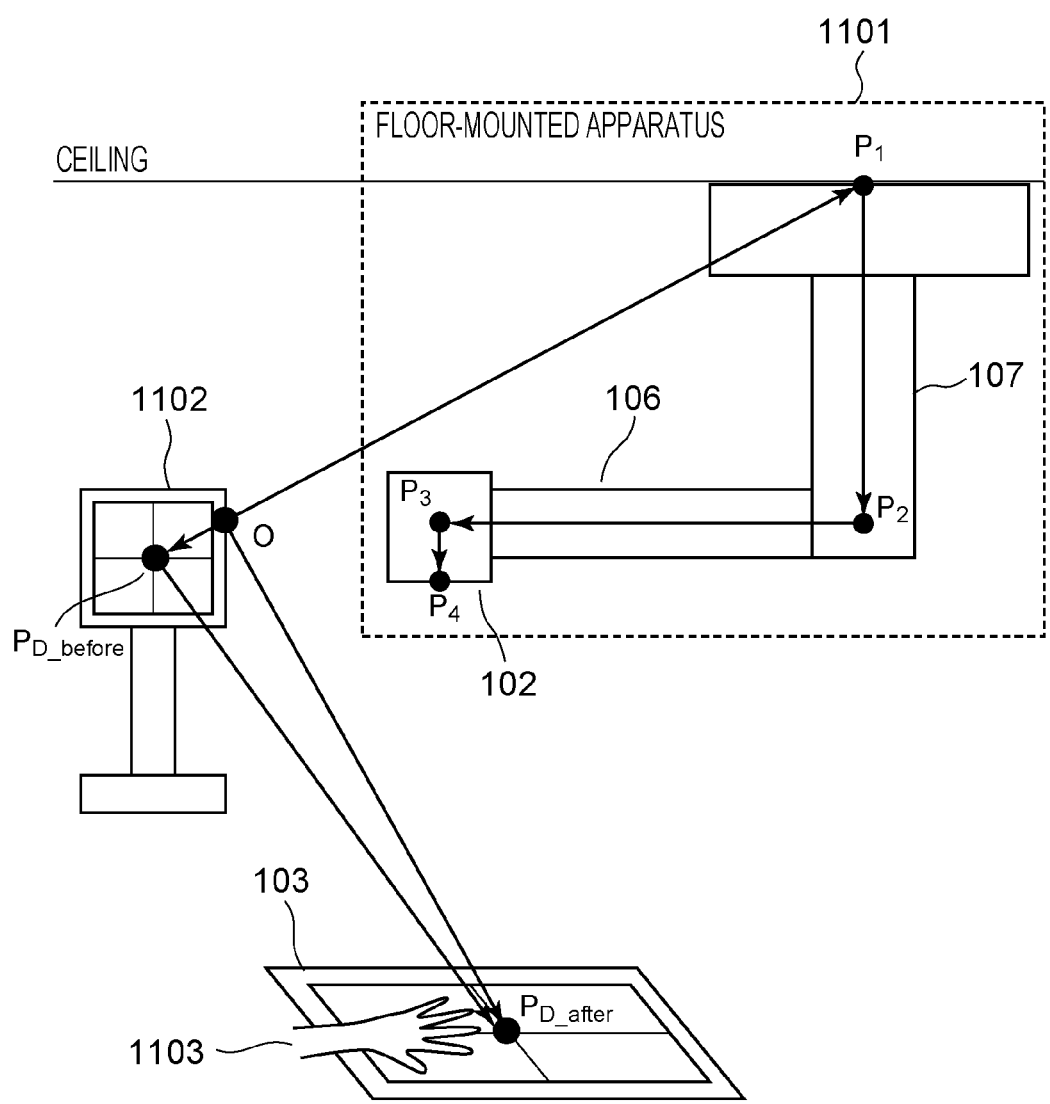
FIG. 12 is a diagram illustrating a configuration example of a radiation imaging apparatus according to a fourth embodiment.

FIG. 12 illustrates an example of the configuration of this embodiment. A characteristic of this embodiment is that a floor-mounted apparatus 1101 is provided instead of the mobile radiography unit 101. The floor-mounted apparatus 1101, like the mobile radiography unit 101, includes a radiation generator 102 and a first arm 106 and a second arm 107 that support the radiation generator 102.

Another characteristic of this embodiment including the floor-mounted apparatus is that a Bucky's radiographic device 1102 is provided instead of the FPD housing unit 110. The Bucky's radiographic device 1102 includes a bucky for moving a grid for preventing scattered ray from entering the FPD 103. The FPD 103 is usually housed in the Bucky's radiographic device 1102 and, in imaging a subject 105, such as a hand, is taken out of the Bucky's radiographic device 1102 for usage.

Like the mobile radiography unit 101, the radiation generator 102 and the FPD 103 are each provided with an acceleration sensor, a gyroscope, or a magnetic sensor. If the vector $OP_1$, which indicates the positional relationship between the Bucky's radiographic device 1102 and the floor-mounted apparatus 1101, is known in advance, the relationship between the orientations of the radiation generator 102 and the FPD 103 can be calculated. Since the positional relationship between the Bucky's radiographic device 1102 and the floor-mounted apparatus 1101 can also be measured at the installation of the individual apparatuses, the vector $OP_1$ can be installed as in the first to third embodiments.

Other examples of a device that has a similar function as the Bucky's radiographic device 1102 include an apparatus (a cradle) that can be charged when joined with the FPD 103 and an apparatus (a check-in apparatus), with which the FPD 103 is brought into contact, when the FPD 103 is brought into a radiography room.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:
1. A radiation imaging apparatus comprising:
a radiation detector configured to detect radiation;
a mobile radiography unit configured to house the radiation detector and including a radiation generator; and
a setting unit configured to set at least one of a reference orientation of the radiation detector for calculating an orientation of the radiation detector and a reference orientation of the radiation generator for calculating an orientation of the radiation generator,
wherein the radiation imaging apparatus is configured to perform radiation imaging to generate an image based on the radiation, and
wherein the setting unit performs the setting in response to determining that the mobile radiography unit stands still, with the radiation detector housed in the mobile radiography unit.
2. The radiation imaging apparatus according to claim 1, wherein the setting unit performs the setting during a period from when protocol information for performing the radiation imaging is set by a user to when movement of the radiation detector is started.
3. The radiation imaging apparatus according to claim 1, wherein the setting unit performs the setting during a period from when protocol information for performing the radiation imaging is set by a user to when a change in the orientation of the radiation generator is started.
4. The radiation imaging apparatus according to claim 1, wherein the setting unit calculates at least one of the reference orientation of the radiation detector and the reference orientation of the radiation generator based on dimensions of the radiation imaging apparatus.
5. The radiation imaging apparatus according to claim 1, further comprising:
a movement measuring unit configured to measure an amount of movement of the mobile radiography unit,
wherein, when the mobile radiography unit moves after the setting, the setting unit corrects or resets the reference orientation of the radiation detector and the reference orientation of the radiation generator based on information from the movement measuring unit.
6. The radiation imaging apparatus according to claim 1, further comprising:
a movement measuring unit configured to measure an amount of movement of the mobile radiography unit,
wherein, when the mobile radiography unit moves after the setting, the setting unit displays at least one of a message that the mobile radiography unit has moved and a message about resetting of the reference orientation on a display of the mobile radiography unit based on information from the movement measuring unit.
7. The radiation imaging apparatus according to claim 1, further comprising an orientation acquisition unit configured to acquire relative relationship between the orientation of the radiation generator and the orientation of the radiation detector.
8. The radiation imaging apparatus according to claim 7, further comprising:
a first orientation measuring unit configured to measure information on the orientation of the radiation generator; and
a second orientation measuring unit configured to measure information on the orientation of the radiation detector,
wherein the orientation acquisition unit acquires the relative relationship based on the reference orientation, a value measured by the first orientation measuring unit, and a value measured by the second orientation measuring unit.

9. The radiation imaging apparatus according to claim 8, wherein the orientation acquisition unit acquires the orientation of the radiation generator from the reference orientation and the value measured by the first orientation measuring unit, acquires the orientation of the radiation detector from the reference orientation and the value measured by the second orientation measuring unit, and determines whether the radiation generator and the radiation detector face each other from the orientation of the radiation generator and the orientation of the radiation detector.

10. The radiation imaging apparatus according to claim 9, wherein the orientation acquisition unit acquires the relative relationship from an angle formed between a first normal vector and a second normal vector, the first normal vector being aligned with a direction of the radiation from the radiation generator and being based on the reference orientation and the value measured by the first orientation measuring unit, the second normal vector being perpendicular to a detector plane of the radiation detector and being based on the reference orientation and the value measured by the second orientation measuring unit.

11. The radiation imaging apparatus according to claim 10, wherein the orientation acquisition unit determines whether the relative relationship is in a range predetermined according to an imaging procedure from the angle formed between the first normal vector and the second normal vector.

12. The radiation imaging apparatus according to claim 11, wherein the range predetermined according to the imaging procedure is any one of whether the detector plane of the radiation detector faces the direction of radiation from the radiation generator, whether a back of the detector plane of the radiation detector faces the direction of radiation from the radiation generator, and whether the radiation generator and the radiation detector are arranged at a predetermined angle.

13. A radiation imaging apparatus comprising:
a radiation detector configured to detect radiation;
a floor or ceiling-mounted apparatus including a radiation generator and an arm configured to move the radiation generator; and
a setting unit configured to set at least one of a reference orientation of the radiation detector for calculating an orientation of the radiation detector and a reference orientation of the radiation generator for calculating an orientation of the radiation generator,
wherein the radiation imaging apparatus is configured to perform radiation imaging to generate an image based on the radiation, and
wherein the setting unit performs the setting in response to determining that the radiation detector unit stands still.

14. The radiation imaging apparatus according to claim 13,
wherein the floor or ceiling-mounted apparatus comprises a Bucky's radiographic device including a bucky for moving a grid for preventing incidence of scattering rays, and
wherein the setting unit performs the setting when the radiation detector is installed at the Bucky's radiographic device.

15. The radiation imaging apparatus according to claim 13,
wherein the floor or ceiling-mounted apparatus is a cradle for charging the radiation detector, and
wherein the setting unit performs the setting when the radiation detector is installed at the cradle.

16. A radiation imaging apparatus comprising:
a radiation detector configured to detect radiation;
a mobile radiography unit configured to house the radiation detector and including a radiation generator;
an orientation acquisition unit configured to acquire relative relationship between an orientation of the radiation generator and an orientation of the radiation detector;
a first orientation measuring unit configured to measure information on the orientation of the radiation generator; and
a second orientation measuring unit configured to measure information on the orientation of the radiation detector,
wherein the radiation imaging apparatus is configured to perform radiation imaging to generate an image based on the radiation, and
wherein the orientation acquisition unit acquires the relative relationship from an angle formed between a first normal vector and a second normal vector, the first normal vector being aligned with a direction of the radiation from the radiation generator and being based on a value measured by the first orientation measuring unit, the second normal vector being perpendicular to a detector plane of the radiation detector and being based on a value measured by the second orientation measuring unit.

17. The radiation imaging apparatus according to claim 16,
wherein the mobile radiography unit includes a display, and
wherein the orientation acquisition unit displays information on arrangement of the radiation generator and the radiation detector on the display based on the relative relationship.

18. The radiation imaging apparatus according to claim 16, wherein the setting unit holds output values from the first orientation measuring unit and the second orientation measuring unit immediately before the setting is performed and performs the setting based on the immediately preceding output values.

19. The radiation imaging apparatus according to claim 16, wherein the first orientation measuring unit includes at least one of an acceleration sensor, an angular velocity sensor, and a geomagnetic sensor.

20. The radiation imaging apparatus according to claim 16, wherein the second orientation measuring unit includes at least one of an acceleration sensor, an angular velocity sensor, and a geomagnetic sensor.

21. The radiation imaging apparatus according to claim 16, further comprising:
a movable apparatus configured to change the orientation of the radiation generator,
wherein the movable apparatus changes the orientation of the radiation generator based on the relative relationship.

22. A radiation detector configured to be housed in a mobile radiography unit including a radiation generator and configured to detect radiation to perform radiation imaging to generate an image based on the radiation, the radiation detector comprising:

a setting unit configured to set at least one of a reference orientation of the radiation detector for calculating an orientation of the radiation detector and a reference orientation of the radiation generator for calculating an orientation of the radiation generator, wherein the setting unit performs the setting in response to determining that the mobile radiography unit stands still, with the radiation detector housed in the mobile radiography unit.

23. A radiation detector configured to be housed in a mobile radiography unit including a radiation generator and configured to detect radiation to perform radiation imaging to generate an image based on the radiation, the radiation detector comprising:

an orientation measuring unit configured to measure information on the orientation of the radiation generator; and an orientation acquisition unit configured to acquire relative relationship between the orientation of the radiation generator and the orientation of the radiation detector, wherein the orientation acquisition unit acquires the relative relationship from an angle formed between a first normal vector and a second normal vector, the first normal vector being aligned with a direction of the radiation from the radiation generator and being based on a value measured by an orientation measuring unit different from the orientation measuring unit, the second normal vector being perpendicular to a detector plane of the radiation detector and being based on a value measured by the orientation measuring unit.

24. A control apparatus configured to control a radiation imaging apparatus including a radiation detector configured to detect radiation and a mobile radiography unit configured to house the radiation detector and including a radiation generator, the radiation imaging apparatus being configured to perform radiation imaging to generate an image based on the radiation, wherein the control apparatus sets at least one of a reference orientation of the radiation detector for calculating an orientation of the radiation detector and a reference orientation of the radiation generator for calculating an orientation of the radiation generator in response to determining that the mobile radiography unit stands still, with the radiation detector housed in the mobile radiography unit.

25. A control apparatus configured to control a radiation imaging apparatus including a radiation detector configured to detect radiation and a mobile radiography unit configured to house the radiation detector and including a radiation generator, the radiation imaging apparatus being configured to perform radiation imaging to generate an image based on the radiation, wherein the control apparatus acquires relative relationship between an orientation of the radiation detector and an orientation of the radiation generator from an angle formed between a first normal vector and a second normal vector, the first normal vector being aligned with a direction of the radiation from the radiation generator and being based on a value calculated by a first orientation measuring unit provided at the radiation generator and measuring information on the orientation of the radiation generator, the second normal vector being perpendicular to a detector plane of the radiation detector and being based on a value calculated by a second orientation measuring unit provided at the radiation detector and measuring information on the orientation of the radiation detector.

26. A method for controlling a radiation imaging apparatus including a radiation detector configured to detect radiation and a mobile radiography unit configured to house the radiation detector and including a radiation generator, the radiation imaging apparatus being configured to perform radiation imaging to generate an image based on the radiation, the method comprising:

setting at least one of a reference orientation of the radiation detector for calculating an orientation of the radiation detector and a reference orientation of the radiation generator for calculating an orientation of the radiation generator in response to determining that the mobile radiography unit stands still, with the radiation detector housed in the mobile radiography unit.

27. A method for controlling a radiation imaging apparatus including a radiation detector configured to detect radiation and a mobile radiography unit configured to house the radiation detector and including a radiation generator, the radiation imaging apparatus being configured to perform radiation imaging to generate an image based on the radiation, the method comprising:

acquiring relative relationship between an orientation of the radiation detector and an orientation of the radiation generator from an angle formed between a first normal vector and a second normal vector, the first normal vector being aligned with a direction of the radiation from the radiation generator and being based on a value calculated by a first orientation measuring unit provided at the radiation generator and measuring information on the orientation of the radiation generator, the second normal vector being perpendicular to a detector plane of the radiation detector and being based on a value calculated by a second orientation measuring unit provided at the radiation detector and measuring information on the orientation of the radiation detector.

28. A non-transitory computer-readable medium storing a program for causing a computer to execute the control method according to claim 26.

* * * * *